US008202288B2

(12) United States Patent
Adams et al.

(10) Patent No.: US 8,202,288 B2
(45) Date of Patent: Jun. 19, 2012

(54) ANGLED TISSUE CUTTING INSTRUMENT HAVING VARIABLY POSITIONABLE CUTTING WINDOW AND INDEXING TOOL FOR USE THEREWITH

(75) Inventors: Kenneth M. Adams, Jacksonville, FL (US); Miro Mitusina, Ruskin, FL (US)

(73) Assignee: Medtronic Xomed, Inc., Louisville, CO (US)

( * ) Notice: Subject to any disclaimer, the term of this patent is extended or adjusted under 35 U.S.C. 154(b) by 860 days.

(21) Appl. No.: 11/897,310

(22) Filed: Aug. 30, 2007

(65) Prior Publication Data

US 2008/0021489 A1  Jan. 24, 2008

Related U.S. Application Data

(62) Division of application No. 10/760,352, filed on Jan. 21, 2004, now Pat. No. 7,276,074.

(51) Int. Cl.
A61B 17/32 (2006.01)

(52) U.S. Cl. ...................................... 606/170

(58) Field of Classification Search ............... 606/170, 606/171, 174, 180, 159; 604/22; 285/381.4, 285/381.5; 403/270, 273
See application file for complete search history.

(56) References Cited

U.S. PATENT DOCUMENTS

| | | | |
|---|---|---|---|
| 177,490 A | 5/1876 | Fones et al. | |
| 4,455,509 A | 6/1984 | Crum et al. | |
| 4,466,429 A | 8/1984 | Loscher et al. | |
| 4,646,738 A | 3/1987 | Trott | |
| 5,152,744 A | 10/1992 | Krause et al. | |
| 5,286,253 A | 2/1994 | Fucci | |
| 5,322,505 A | 6/1994 | Krause et al. | |
| 5,411,514 A | 5/1995 | Fucci et al. | |
| 5,437,630 A | 8/1995 | Daniel et al. | |
| 5,529,580 A | 6/1996 | Kusimoki et al. | |
| 5,540,708 A * | 7/1996 | Lim et al. | 606/170 |
| 5,601,586 A | 2/1997 | Fucci et al. | |
| 5,620,415 A | 4/1997 | Lucey et al. | |
| 5,620,447 A | 4/1997 | Smith et al. | |
| 5,690,660 A | 11/1997 | Kauker et al. | |
| 5,704,534 A | 1/1998 | Huitema et al. | |
| 5,807,277 A * | 9/1998 | Swaim | 606/170 |
| 5,922,003 A | 7/1999 | Anctil et al. | |
| 5,961,532 A * | 10/1999 | Finley et al. | 606/170 |
| 6,136,004 A | 10/2000 | Keller | |
| RE38,018 E | 3/2003 | Anctil et al. | |

* cited by examiner

Primary Examiner — Kevin T Truong

(57) ABSTRACT

An angled tissue cutting instrument includes an outer member having an elongate body with a bend and a forward end, and a distal tip rotatably mounted on the forward end. The distal tip and body are rotatable relative to one another about a central longitudinal axis of the tip to variably position a cutting window of the tip in a selected directional position about the axis. Relative rotation between the distal tip and the body about the axis is prevented to lock the cutting window in a selected directional position when the outer member is maintained in a longitudinally extended position by an inner member of the instrument disposed within the outer member. An indexing tool for the angled tissue cutting instrument has a socket for receiving the distal tip to effect rotational indexing. A method of variably positioning a cutting window of an angled tissue cutting instrument involves rotationally indexing a distal tip of an outer member of the instrument and maintaining the distal tip in a selected rotationally indexed position.

42 Claims, 12 Drawing Sheets

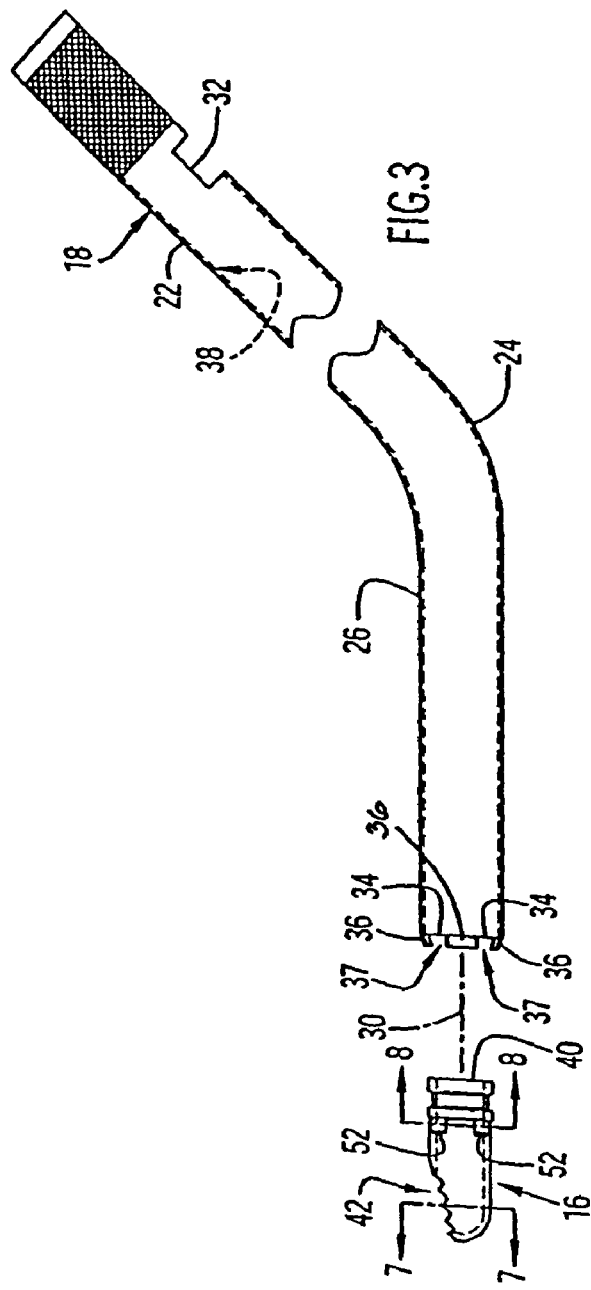
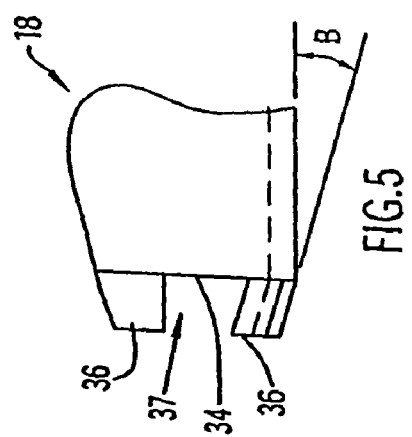
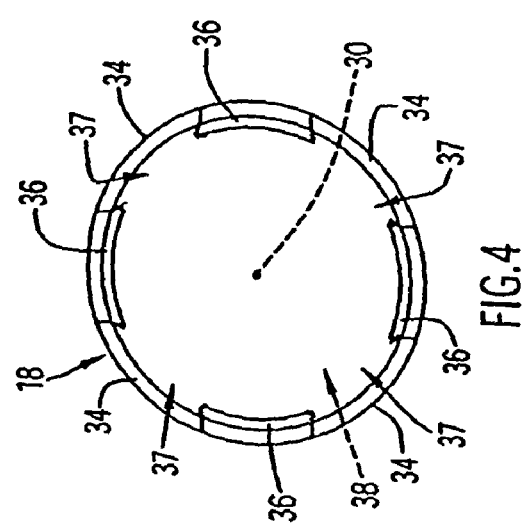

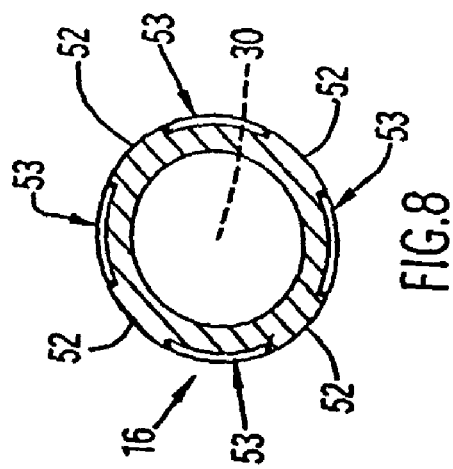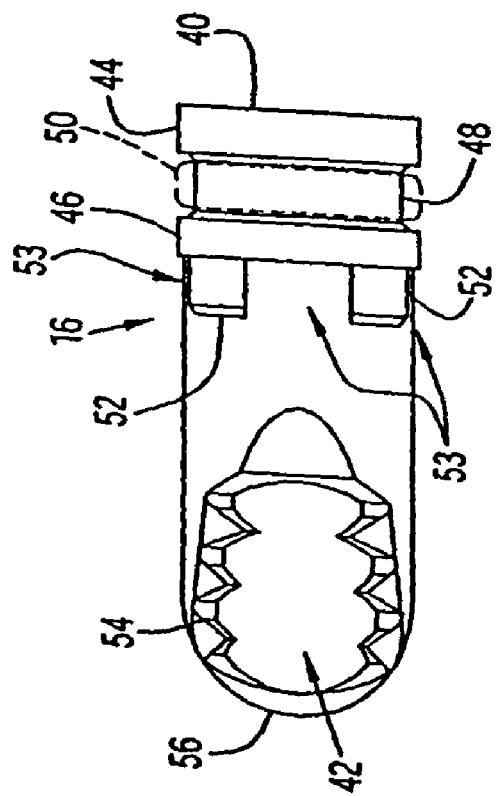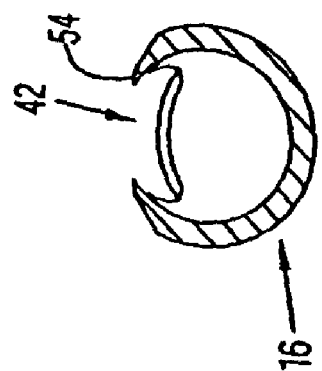

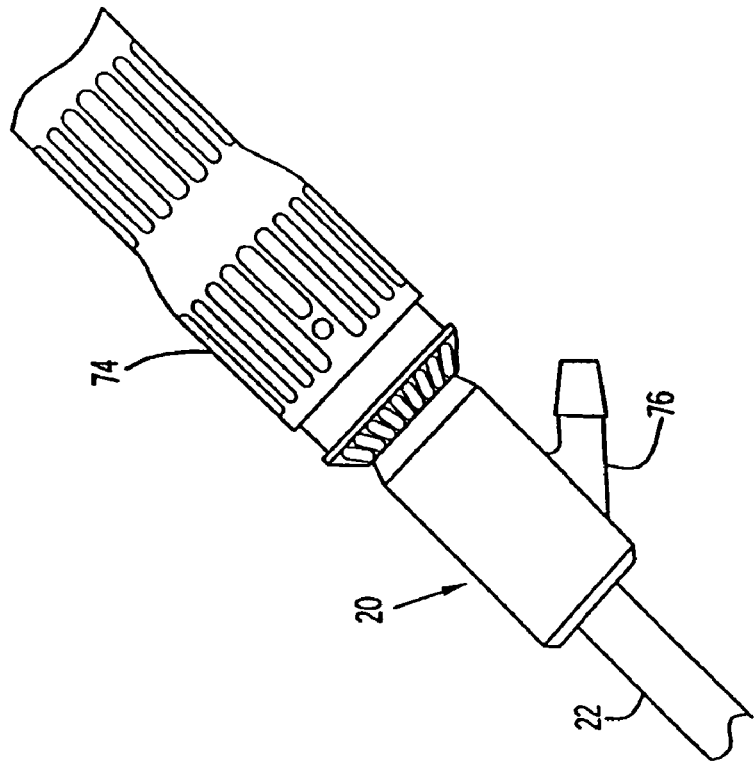
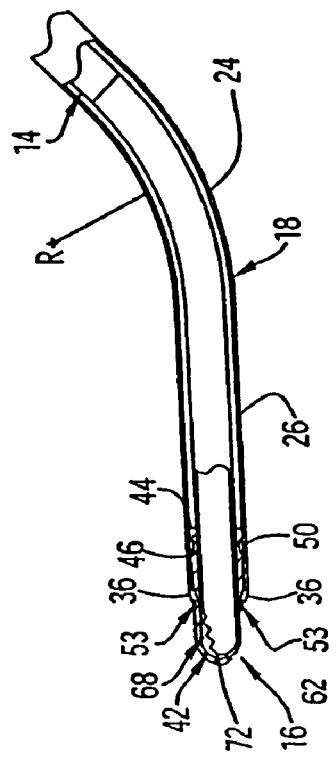
FIG. 11

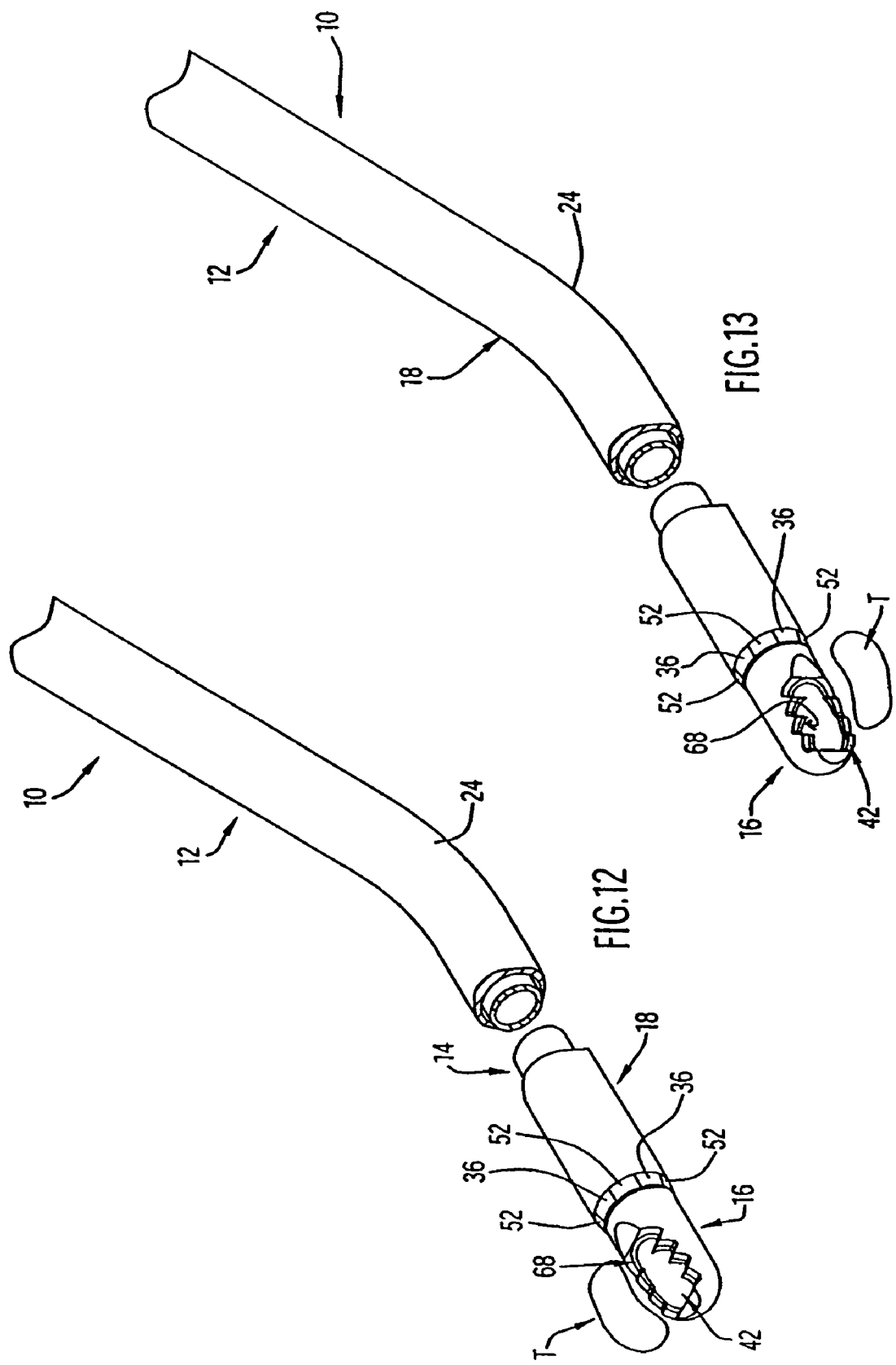

ANGLED TISSUE CUTTING INSTRUMENT HAVING VARIABLY POSITIONABLE CUTTING WINDOW AND INDEXING TOOL FOR USE THEREWITH

CROSS-REFERENCE TO RELATED PATENT APPLICATION

This application is a divisional of prior U.S. patent application Ser. No. 10/760,352 filed Jan. 21, 2004 now U.S. Pat. No. 7,276,074, the entire disclosure of which is incorporated herein by reference.

BACKGROUND OF THE INVENTION

1. Field of the Invention

The present invention relates generally to angled tissue cutting instruments including an elongate outer member having a bend and a distal end with a cutting window and, more particularly, to angled tissue cutting instruments in which the cutting window is variably positionable relative to the bend, to indexing tools for variably positioning the cutting windows of angled tissue cutting instruments, and to methods of variably positioning a cutting window of an angled tissue cutting instrument.

2. Brief Discussion of the Related Art

Tissue cutting instruments comprising an elongate outer tubular member and an elongate inner member rotatably disposed in the outer tubular member to cut anatomical tissue have become well-accepted for use in various surgical procedures. Typically, the inner member has a distal end with a cutting edge and the outer member has a distal end with a cutting window through which the cutting edge is exposed to cut anatomical tissue when the inner member is rotated within the outer member. The cutting edge may have various configurations in accordance with the type of tissue and/or the type of cutting action to be accomplished. In some instances, the distal end of the outer member has a cutting edge cooperable with the cutting edge of the inner member to cut the anatomical tissue as the inner member is rotated. The outer and inner members ordinarily have proximal ends adapted for coupling with a powered surgical handpiece used to rotate the inner member relative to and within the outer member. Many tissue cutting instruments provide for aspiration of anatomical debris through the tissue cutting instrument and/or irrigation at the operative or cutting site via an irrigating or flushing fluid supplied along the tissue cutting instrument.

In tissue cutting instruments of the foregoing type, the outer members may be longitudinally or axially straight or may be longitudinally or axially bent, angled or curved. Depending on the location of the cutting site in the patient's body, angled tissue cutting instruments may better facilitate positioning of the outer member distal end at the cutting site while the handpiece remains external to the patient's body so as to provide better access to the cutting site from externally of the patient's body. The bent, angled or curved outer members of angled tissue cutting instruments typically include a proximal length portion extending distally to a bend, angle or curve and a distal length portion extending distally from the bend, angle or curve to the distal end. Where the outer member is longitudinally or axially bent, angled or curved, the inner member is normally provided with a flexible region adjacent the bend, angle or curve in the outer member whereby the inner member conforms to the longitudinally or axially bent, angled or curved configuration of the outer member while still being rotatable within the outer member. Angled tissue cutting instruments of the latter type are represented by U.S. Pat. No. 177,490 to Fones, U.S. Pat. No. 4,445,509 to Auth, U.S. Pat. No. 4,466,429 to Loscher, U.S. Pat. No. 4,646,738 to Trott, U.S. Pat. No. 5,152,744 and U.S. Pat. No. 5,322,505 to Krause et al, U.S. Pat. Nos. 5,286,253, 5,411,514 and U.S. Pat. No. 5,601,586 to Fucci et al, U.S. Pat. No. 5,437,630 to Daniel et al, U.S. Pat. No. 5,529,580 to Kusumoki et al, U.S. Pat. No. 5,620,415 to Lucy et al, U.S. Pat. No. 5,620,447 to Smith et al, and U.S. Pat. No. 5,922,003 to Anctil et al.

In most angled tissue cutting instruments, the bend, curve or angle is formed in an elongate body of the outer member as part of the manufacturing or fabrication process and is essentially rigid or fixed. The distal end of the outer member is also ordinarily fixed to the elongate body such that the position of the cutting window relative to the bend, curve or angle is fixed and cannot be varied or adjusted. Accordingly, the outer members of angled tissue cutting instruments are normally provided with a cutting window in a fixed rotational position about a central longitudinal axis of the distal end such that the cutting window faces in a fixed, predetermined direction relative to the bend. This situation presents disadvantages where access to an operative or cutting site is best established with the bend extending in a particular direction or orientation but the fixed position of the cutting window relative to the bend in the particular direction or orientation does not face the anatomical tissue intended to be cut with the instrument at the operative site. While it is possible to rotate the entire instrument to enable the cutting window to face the anatomical tissue intended to be cut, the direction or orientation of the bend is necessarily changed thereby and no longer extends in the particular direction or orientation needed to best establish access to the operative site. Use of the instrument with the cutting window facing the anatomical tissue intended to be cut but with the bend extending in a different direction or orientation may be prohibited due to the presence of anatomical structure at risk of being traumatized due to contact with the instrument. Also, rotation of the entire instrument results in the handpiece being correspondingly rotated, such that the handpiece may no longer be oriented for proper grasping and manipulation by the surgeon.

U.S. Pat. No. 5,601,586 and No. 5,411,514 to Fucci et al are representative of variable angle tissue cutting instruments in which a longitudinally straight outer member has a spiral relief cut forming a non-rigid bendable section along which the outer member may be bent axially by a user, and the inner member is flexible to follow the bent configuration of the outer member. By bending the outer member along the bendable section, a cutting window at the distal end of the outer member can be positioned to face in various directions. Directional positioning of the cutting window cannot be accomplished without bending the bendable section and the distal end cannot be rotationally indexed about its central longitudinal axis. The longitudinal profile of the outer member cannot be maintained and still allow variable directional positioning of the cutting window.

U.S. Pat. No. 5,620,447 to Smith et al relates to an angled tissue cutting instrument in which the outer member has a bendable section formed by a spiral relief cut and is also rotatable about its longitudinal axis to position a cutting window at a distal end thereof in various selected angular positions. The entire outer member must be rotated about its axis in order to vary the angular position of the cutting window. Rotation of the outer member is effected at and with respect to a base at a proximal end of the outer member, the bendable section being necessary to transmit this rotational torque to correspondingly rotate the distal end. A rigid intermediate member having a fixed bend is required between the inner member and the bendable section of the outer member. The bendable section and the intermediate member add undesired structural and functional complexity and cost to the instrument. The base at the proximal end of the outer member requires specialized structure precluding the use of a conventional hub at the proximal end of the outer member.

In view of the foregoing deficiencies of the prior art, a need exists for an angled tissue cutting instrument in which the distal end and elongate body of the outer member are rotatable relative to one another to permit selective rotational indexing of the distal end about its central longitudinal axis to variably position the cutting window of the distal end. A need further exists for an angled tissue cutting instrument providing selective directional or angular positioning of the cutting window relative to a bend, angle or curve in the elongate body of the outer member without requiring rotation of the entire outer member and/or rotation of the entire instrument. There is also a need for an angled tissue cutting instrument that permits selective directional or angular positioning of the cutting window relative to a rigid or fixed bend, angle or curve in a one-piece elongate body of the outer member. An additional need prevails for an angled tissue cutting instrument in which the outer member is movable between a longitudinally extended position wherein the distal end and elongate body of the outer member are prevented from rotating relative to one another about a central longitudinal axis of the distal end and a longitudinally retracted position wherein the distal end and elongate body are rotatable relative to each other about the central longitudinal axis to rotationally index the distal end. A still further need exists for an angled tissue cutting instrument in which distal advancement of the inner member in the outer member a full insertion distance locks the cutting window of the outer member in a selected directional position while retraction or withdrawal of the inner member proximally from its full insertion distance unlocks the cutting window for rotational indexing to another selected directional position. There is also a need for an indexing tool for rotationally indexing a distal end of an outer member so that the fingers of a person's hand do not contact the distal end and particularly do not contact sharp cutting edges on and/or exposed from the distal end. Moreover, there is a need for a kit supplying both an angled tissue cutting instrument having a variably positionable cutting window and an indexing tool for variably positioning the cutting window. Another need exists for a method of variably positioning a cutting window at a distal end of an outer member of an angled tissue cutting instrument by rotationally indexing the distal end by rotating it about its central longitudinal axis relative to an elongate body of the outer member, as permitted by relative longitudinal movement between the distal end and elongate body.

SUMMARY OF THE INVENTION

Accordingly, it is an object of the present invention to overcome the aforementioned disadvantages of prior angled tissue cutting instruments.

Another object of the present invention is to permit selective relative rotation between a distal end and elongate body of an outer member of an angled tissue cutting instrument about a central longitudinal axis of the distal end to adjustably position a cutting window of the distal end.

A further object of the present invention is to effect relative rotation between a distal end and elongate body of an outer member of an angled tissue cutting instrument about a central longitudinal axis of the distal end to position a cutting window of the distal end at various rotational positions about the central longitudinal axis.

It is also an object of the present invention to selectively adjust the directional or angular orientation of a cutting window in a distal end of an outer member of an angled tissue cutting instrument relative to a bend in an elongate body of the outer member rotatably mounting the distal end.

The present invention also has as an object to prevent relative rotation between a distal end and elongate body of an outer member of an angled tissue cutting instrument when the outer member is in a longitudinally extended position and to permit relative rotation between the distal end and elongate body when the outer member is in a longitudinally retracted position to variably position a cutting window of the distal end.

Moreover, it is an object of the present invention to utilize relative longitudinal movement between a distal end and elongate body of an outer member of an angled tissue cutting instrument to selectively prevent and selectively permit rotational indexing of the distal end.

The present invention has as an additional object to prevent relative rotation between a distal end and elongate body of an outer member of an angled tissue cutting instrument about a central longitudinal axis of the distal end when an inner member of the instrument is disposed within the outer member a full insertion distance and to permit relative rotation between the distal end and elongate body about the central longitudinal axis when the inner member is retracted from its full insertion distance.

It is also an object of the present invention to lock the outer member of an angled tissue cutting instrument in a longitudinally extended position preventing relative rotation between a distal end and elongate body of the outer member in response to an inner member of the instrument being disposed within the outer member a full insertion distance and to release the outer member for movement to a longitudinally retracted position permitting relative rotation between the distal end and elongate body in response to the inner member being retracted from the full insertion distance.

An additional object of the present invention is to allow a single angled tissue cutting instrument to access an operative site with a bend of an outer member of the instrument extending in a particular direction and to cut anatomical tissue at different directional locations at the operative site via a cutting window in a distal end of the outer member without changing the particular direction for the bend.

Yet another object of the present invention is to accomplish rotational indexing of a distal end of an outer member of an angled tissue cutting instrument about a central longitudinal axis of the distal end without rotating the entire outer member or the entire instrument.

The present invention has as a further object to provide an indexing tool by which a distal end of an outer member of an angled tissue cutting instrument can be moved proximally and rotated relative to an elongate body of the outer member without a person's hand contacting the distal end.

The present invention also has as an object to provide an indexing tool for mechanically applying the forces needed to move an outer member of an angled tissue cutting instrument from a longitudinally extended position to a longitudinally retracted position and to rotationally index a distal end of the outer member.

Another object of the present invention is to make available a kit comprising an angled tissue cutting instrument and an indexing tool for rotationally indexing a distal end of the outer member of the angled tissue cutting instrument to adjust the position of a cutting window in the distal end.

The aforesaid objects are achieved individually and in combination, and it is not intended that the present invention be construed as requiring two or more of the objects to be combined unless expressly required by the claims attached hereto.

Some of the advantages of the present invention are that directional positioning of the cutting window is accomplished without requiring a flexible bendable section in the elongate body of the outer member; the elongate body can be fabricated as one-piece with a rigid bend; the elongate body of the outer member may include a plurality of bends extending in the same or different directions and at the same or different angles; the same instrument can be used to cut anatomical tissue located medially, laterally, superiorly and inferiorly to the distal end of the outer member positioned at an operative site with a bend of the outer member extending in a particular direction to access the operative site; standard hubs can be used to mount the proximal ends of the outer and inner members; the angled tissue cutting instrument does not require an intermediate member between the inner and outer members; the distal end may be locked in various rotationally indexed positions; various types of engagement structure can be provided in the angled tissue cutting instrument for preventing relative rotation between the distal end and elongate body in the longitudinally extended position for the outer member; the distal end may be a one-piece member or may be formed of multiple parts; selective directional positioning of the cutting window can be accomplished quickly and reliably during surgery; the risk of a surgical glove being unintentionally torn by a cutting edge of the instrument is avoided since the indexing tool avoids contact of the gloved hand with the outer member distal end; proper placement of the indexing tool on the distal end of the outer member is ensured; the indexing tool is easy to use; various inner members conventionally used in angled tissue cutting instruments may be used as the inner member of the angled tissue cutting instrument of the present invention; the inner member can be retracted from the full insertion distance while remaining within the outer member such that the inner member does not have to be fully withdrawn from the outer member to permit rotational indexing of the outer member distal end; the inner member remaining within the outer member in the longitudinally retracted position for the outer member controllably limits retraction of the distal end within the elongate body in the longitudinally retracted position; extension of the distal end from the elongate body in the longitudinally extended position is also controlled to prevent detachment of the distal end from the elongate body; depending on how the inner and outer members are coupled to the handpiece, retraction of the inner member from its full insertion distance may be accomplished while the inner and outer members are detached from the handpiece or while the inner and outer members remain attached to the handpiece; the angled tissue cutting instrument may be provided with or without an aspiration passage; the angled tissue cutting instrument may be provided with or without an irrigation passage; and leakage of irrigation fluid may be prevented via a seal between the distal end and elongate body.

These and other objects, advantages and benefits are realized with the present invention as generally characterized in an angled tissue cutting instrument comprising an outer member and an inner member movably disposed in the outer member. The outer member includes a distal end or tip rotatably mounted to a forward end of an elongate body having a bend. The distal tip has a central longitudinal axis and a cutting window from which a cutting tip of the inner member is exposed to cut anatomical tissue when the inner member is moved within the outer member. The distal tip and body are selectively rotatable relative to one another about the central longitudinal axis to variably position the cutting window in a selected one of a plurality of directional positions about the central longitudinal axis. Relative rotation between the distal tip and the elongate body about the central longitudinal axis is prevented to lock the cutting window in a selected directional position when the outer member is in a longitudinally extended position. Relative rotation between the distal tip and the elongate body about the central longitudinal axis is permitted when the outer member is in a longitudinally retracted position to permit rotational indexing of the distal tip to position the cutting window in another selected one of the directional positions.

Engagement structure is provided in the instrument to prevent relative rotation between the distal tip and the body when the outer member is in the longitudinally extended position. In one embodiment, the engagement structure comprises body engagement structure including a plurality of body protrusions and body slots on the elongate body cooperatively interengageable with tip engagement structure including a plurality of tip slots and tip protrusions, respectively, on the distal tip. Cooperative interengagement between the body engagement structure and the tip engagement structure prevents relative rotation between the distal tip and the elongate body about the central longitudinal axis. The body engagement structure is cooperatively interengaged with the tip engagement structure when the outer member is in the longitudinally extended position and is disengaged from the tip engagement structure when the outer member is in the longitudinally retracted position.

The longitudinally extended and longitudinally retracted positions are obtained via relative longitudinal movement between the distal tip and the elongate body. In the longitudinally extended position, the distal tip is extended longitudinally distally from the forward end of the elongate body and, in the longitudinally retracted position, the distal tip is retracted longitudinally proximally relative to the elongate body. The outer member may be placed in the longitudinally extended position in response to distal advancement of the inner member within the outer member to a full insertion distance, causing distal extension of the distal tip from the elongate body. The outer member may be maintained or locked in the longitudinally extended position by the outer member and the inner member being releasably attached to a handpiece. The inner member may be withdrawn or moved proximally relative to the elongate body of the outer member a sufficient distance from its full insertion distance so that relative longitudinal movement is permitted between the distal tip and the elongate body by which the outer member may be placed in the longitudinally retracted position. The cutting window is maintained in a selected directional position by moving the outer member from the longitudinally retracted position to the longitudinally extended position. Movement of the outer member from the longitudinally retracted position to the longitudinally extended position may be accomplished in response to distal advancement of the inner member the full insertion distance within the outer member, thereby causing the body engagement structure to cooperatively interengage with the tip engagement structure with the cutting window in the selected directional position. Where the outer and inner members have been detached from the handpiece, reattachment of the outer and inner members to the handpiece secures the outer member in the longitudinally extended position in which the engagement structure prevents relative rotation between the distal tip and the elongate body about the central longitudinal axis.

The present invention is also generally characterized in an indexing tool for use with an angled tissue cutting instrument that has an outer member including an elongate body and a distal tip with a cutting window. The indexing tool comprises a retention element, a handle extending from the retention element, and external indicia. The retention element has a central longitudinal axis and a socket for removably receiving the distal tip of the outer member of the angled tissue cutting instrument. The socket has a configuration to mate with an external configuration of the distal tip when the distal tip is in an insertion orientation relative to the socket. The external indicia of the indexing tool is alignable with the cutting window of the distal tip to obtain the insertion orientation. The handle is movable to move the retention element longitudinally along its central longitudinal axis to apply axial force to the distal tip received in its socket by which the distal tip is retracted proximally relative to the elongate body of the outer member. The handle is movable to move the retention element rotationally about its central longitudinal axis to apply rotational force to the retracted distal tip received in the socket by which the distal tip is rotated relative to the elongate body to effect rotational indexing of the cutting window.

The present invention is additionally characterized in an angled tissue cutting instrument kit comprising an angled tissue cutting instrument and an indexing tool. The angled tissue cutting instrument includes an elongate outer member and an elongate inner member movably disposed in the outer member. The outer member includes an elongate body having a bend and a forward end, and a distal tip mounted on the forward end. The distal tip has a central longitudinal axis and a cutting window radial to the central longitudinal axis. The distal tip is movable longitudinally relative to the elongate body from a longitudinally extended position to a longitudinally retracted position in response to axial force on the distal tip. The distal tip is rotatable relative to the elongate body about its central longitudinal axis in the longitudinally retracted position to adjust the radial position of the cutting window about the axis in response to rotational force on the distal tip. The distal tip is prevented from rotating relative to the elongate body in the longitudinally extended position to lock the cutting window in a selected radial position about the axis. The indexing tool comprises a retention element having a socket for removably receiving the distal tip and a handle extending from the retention element. The indexing tool is movable via the handle to apply the axial force on the distal tip to move the distal tip from the longitudinally extended position to the longitudinally retracted position and to apply the rotational force on the distal tip to rotate the distal tip relative to the elongate body about the central longitudinal axis. The socket preferably has a configuration to mate with an external configuration of the distal tip in an insertion orientation. Preferably, the indexing tool comprises external indicia, and the insertion orientation for the distal tip corresponds to alignment of the cutting window with the indicia.

The present invention is further generally characterized in a method of variably positioning the cutting window of an angled tissue cutting instrument, comprising the steps of effecting relative rotation between a distal tip and an elongate body of an outer member of the angled tissue cutting instrument about a central longitudinal axis of the distal tip with the outer member in a longitudinally retracted position to move a cutting window of the distal tip to a selected directional position about the axis, advancing an inner member of the angled tissue cutting instrument distally within the outer member with the cutting window in the selected directional position to move the outer member to a longitudinally extended position, preventing relative rotation between the distal tip and the elongate body about the central longitudinal axis in response to the step of advancing, and locking the outer member in the longitudinally extended position such that the cutting window is locked in the selected directional position. Effecting relative rotation between the distal tip and the elongate body may be preceded by the steps of moving the outer member from the longitudinally extended position to the longitudinally retracted position and disengaging tip engagement structure on the distal tip from body engagement structure on the body in response to the step of moving. The step of moving may involve withdrawing the inner member proximally within the outer member and retracting the distal tip proximally relative to the elongate body. The step of advancing may involve extending the distal tip distally from the elongate body. The step of preventing relative rotation may include engaging the tip engagement structure with the body engagement structure. The step of locking may include releasably attaching proximal ends of the outer and inner members to a handpiece.

Other objects, features and advantages of the present invention will become apparent from the following description of the preferred embodiment taken in conjunction with the accompanying drawings, wherein like parts in each of the several figures are identified by the same reference characters.

BRIEF DESCRIPTION OF THE DRAWINGS

FIG. 3 is a broken, exploded side view of an outer member of the angled tissue cutting instrument.

FIG. 4 is a forward end view of an elongate body of the outer member.

FIG. 5 is an enlarged fragmentary view of the forward end of the elongate body.

FIG. 6 is a top view of a distal tip of the outer member.

FIG. 7 is a sectional view of the distal tip taken along line 7-7 of FIG. 3.

FIG. 8 is a sectional view of the distal tip taken along line 8-8 of FIG. 3.

FIG. 11 is a broken longitudinal sectional view of the instrument illustrating the outer member locked in the longitudinally extended position subsequent to rotational indexing of the distal tip.

FIG. 12 is a broken perspective view showing the distal tip locked in a first rotational position about the central longitudinal axis.

FIG. 13 is a broken perspective view illustrating the distal tip locked in a second rotational position about the central longitudinal axis.

DESCRIPTION OF THE PREFERRED EMBODIMENTS

Figure 1:
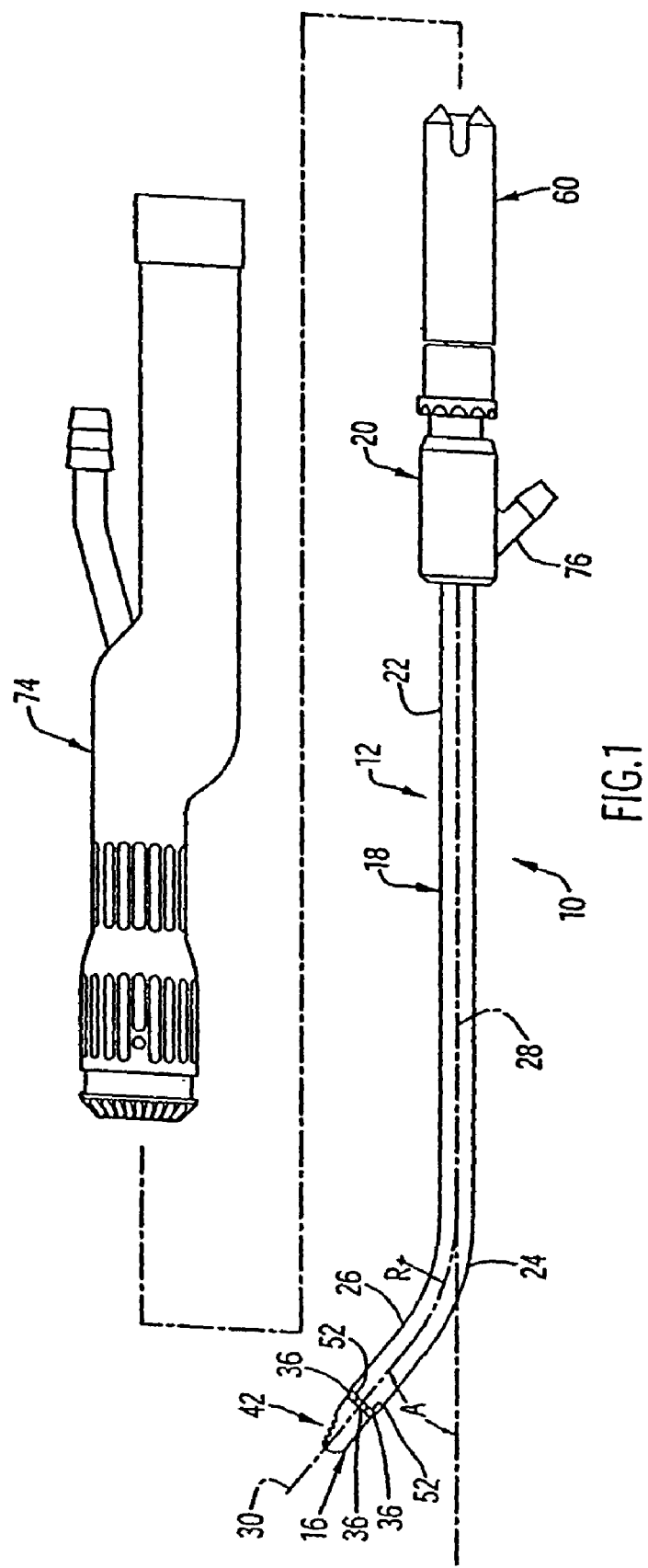
FIG. 1 is a side view of an angled tissue cutting instrument according to the present invention shown in exploded relation to a handpiece.
Figure 2:
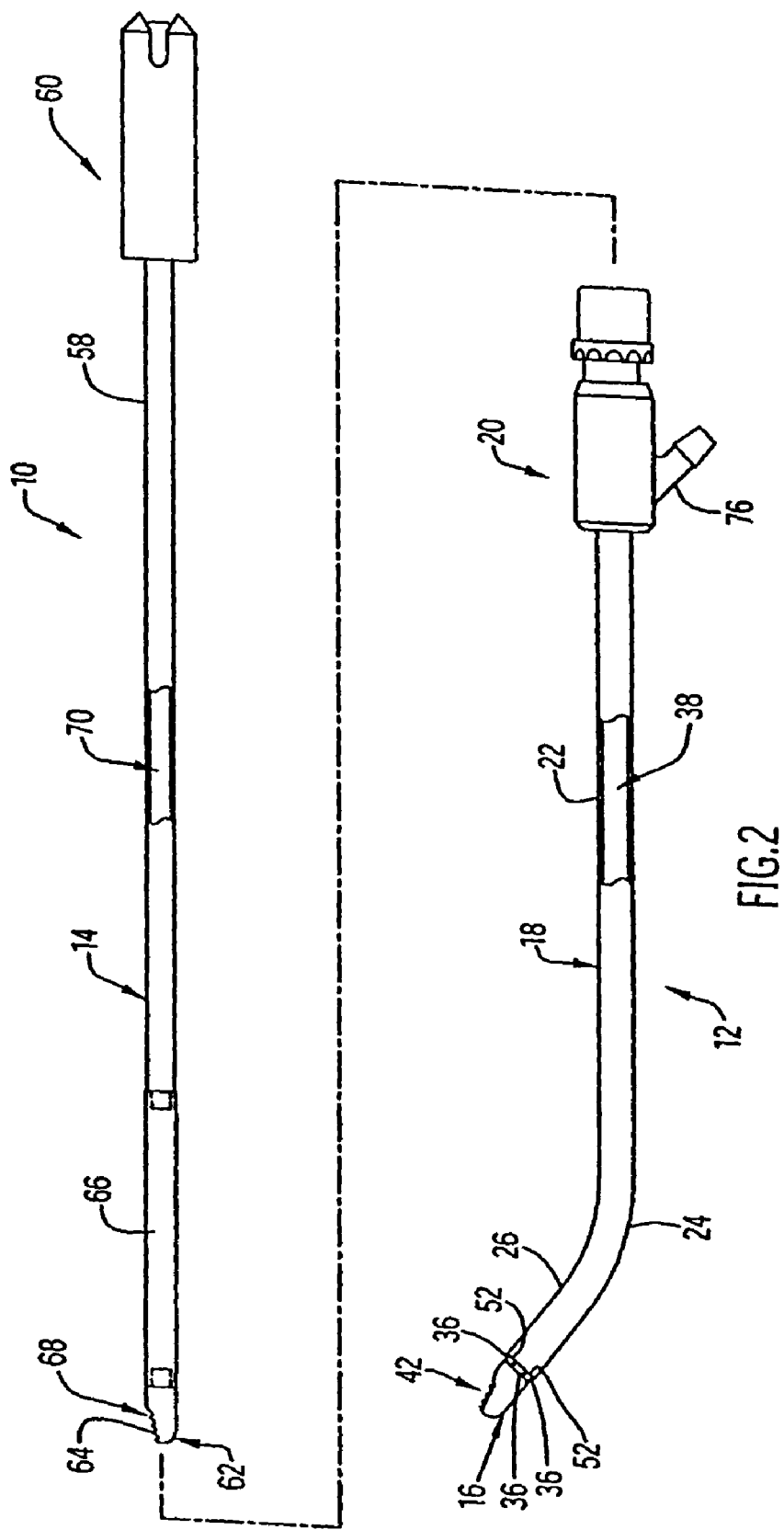
FIG. 2 is a broken, exploded side view of the angled tissue cutting instrument.

An angled tissue cutting instrument or blade 10 is illustrated in FIGS. 1 and 2 and includes an elongate outer tubular member 12 and an elongate inner member 14 rotatably or movably disposed within the outer member. Outer member 12, which may be considered an outer blade member, includes a distal end or tip 16 and an elongate body 18 having a forward end rotatably mounting distal tip 16. Body 18 has a rearward or proximal end coupled to an outer member hub 20, a proximal length portion 22 extending distally from outer member hub 20 to a bend, curve or angle 24, and a distal length portion 26 extending distally from bend 24 to the forward end at an angle A relative to a central longitudinal axis 28 of the proximal length portion. The proximal and distal length portions 22 and 26 are each shown as having a longitudinally or axially straight configuration with angle A defined between a central longitudinal axis 30 of the distal length portion and the central longitudinal axis 28 of the proximal length portion. However, it should be appreciated that the proximal and distal length portions can have various non-straight configurations including one or more additional bends, curves or angles. The bend 24 is essentially rigid or fixed, with the body 18 being essentially a rigid, one-piece member formed by bending a continuous and unbroken tubular member of solid wall construction to pre-form the bend 24 therein during the fabrication or manufacturing process. The angle A, radius of curvature R and location of the bend 24 may vary depending on the surgical procedure in which the angled tissue cutting instrument is to be used, and the outer diameter of the body 18 may also vary. Representative but not limiting angles A for the bend 24 include 12°, 40°, 45° and 60°. Where the elongate body 18 has more than one bend, the bends may extend in the same direction or in different directions from one another and may have the same angle or different angles from one another.

As best shown in FIG. 3, the proximal end of elongate body 18 may be knurled to facilitate attachment to outer member hub 20. An inlet port 32 may be formed in the proximal end of the body 18 for communication with an irrigation port of a powered surgical handpiece as explained further below. The body 18 comprises body engagement structure selectively cooperatively interengageable with tip engagement structure of distal tip 16 to prevent relative rotation between the tip and body about axis 30. The body engagement structure is depicted by way of example as comprising body protrusions and slots for selectively cooperatively interengaging tip slots and protrusions, respectively, depicted by way of example as forming the tip engagement structure. However, it should be appreciated that the body engagement structure and the tip engagement structure can be designed in various ways. As best shown in FIGS. 3-5, the forward end of body 18 has a plurality of arcuately or circumferentially extending edge segments 34 in a plane perpendicular to axis 30 and a plurality of arcuately or circumferentially extending body protrusions or keys 36 extending distally or forwardly from the edge segments 34 at an angle in the direction of axis 30. The body protrusions 36 are spaced from one another at radial locations about the axis 30, and the edge segments 34 are disposed between the body protrusions to define an arcuately or circumferentially extending body slot or keyway 37 between each pair of radially adjacent body protrusions. Although the number of edge segments 34 and body protrusions 36 may vary, body 18 is illustrated by way of example as having four body protrusions 36 at 90° spaced radial locations about the axis 30 and four edge segments 34 alternatingly arranged with the body protrusions about the axis 30 such that the body slots 37 are also spaced 90° from one another.

The forward end of body 18 has an opening in the plane of edge segments 34 communicating and coaxial with the lumen 38 through body 18. The body 18 is of uniform outer diameter and uniform inner diameter between the proximal end and edge segments 34, and the lumen 38 is of uniform diameter. The body protrusions 36 extend angularly inwardly from the edge segments 34 in the forward or distal direction to terminate at arcuately or circumferentially extending forward edges, and the forward edges of the body protrusions 36 circumscribe an opening coaxial with lumen 38. The inner surfaces of the body protrusions 36 thusly circumscribe an area of circular cross-section tapering in diameter from the edge segments 34 to the forward edges of the body protrusions. The angle at which the body protrusions 36 extend inwardly from the edge segments 34 may vary, but in one embodiment the body protrusions extend inwardly at an angle B of about 15° to the outer diameter of body 18 at edge segments 34 as best seen in FIG. 5.

As best shown in FIGS. 3 and 6-8, the distal tip 16 is hollow and has an open rearward or proximal end 40 slidably and rotatably received in the open forward end of body 18 and has a cutting window 42 located distally of the forward end of body 18 when the outer member 12 is in a longitudinally extended position as explained further below. The cutting window 42 has a plurality of directional positions facing radially, angularly or laterally outwardly or transverse to the central longitudinal axis 30, and the cutting window communicates with the interior of the distal tip 16. The distal tip 16 is slidably and rotatably mounted to the forward end of body 18 coaxial with the distal length portion 26 such that the central longitudinal axis of the distal tip 16 is defined by the central longitudinal axis 30 of the distal length portion. The distal tip 16 has a plurality of rotational, directional or angular positions about the central longitudinal axis 30 corresponding to the directional positions for cutting window 42 as explained further below.

The distal tip 16 includes a rearward annular shoulder 44 at rearward end 40 and a forward annular shoulder 46 spaced forwardly from the rearward shoulder 44 so as to be disposed between the rearward shoulder and the cutting window 42. The rearward and forward shoulders 44 and 46 are spaced longitudinally from one another by a cylindrical segment 48 of tip 16 having an outer diameter smaller than the outer diameters of the shoulders 44 and 46. The outer diameters of the shoulders 44 and 46 are selected to be received within the lumen 38 of elongate body 18 with a close fit while still permitting relative longitudinal sliding movement between the distal tip 16 and body 18 along the axis 30 as well as relative rotation between the distal tip and body about axis 30. A seal 50, such as an annular or O-ring seal of appropriate thickness, may be disposed around the cylindrical segment 48 to prevent leakage of irrigation fluid from the outer member as explained further below.

A plurality of arcuately or circumferentially extending tip protrusions 52 extend longitudinally forwardly or distally from the forward shoulder 46 to terminate at forward edges of the tip protrusions. Outer surfaces of the tip protrusions 52 define arcuate or circumferential segments of a circle having a diameter and circumference between forward shoulder 46 and the forward edges of the tip protrusions 52 such that the tip protrusions define raised keys along the outer surface of the distal tip 16 distally or forwardly of the forward shoulder 46 as best shown by FIGS. 3, 6 and 8. The tip protrusions 52 are spaced from one another at radial locations about the axis 30 by arcuately or circumferentially extending tip slots or keyways 53. The arcuate or circumferential width of the tip protrusions or keys 52 is selected to be received in the width of the body slots or keyways 37 with a mating or complementary fit, and the arcuate or circumferential width of the tip slots or keyways 53 is selected to receive the width of the body protrusions or keys 36 with a mating or complementary fit to prevent or lock the distal tip 16 and elongate body 18 against rotation relative to one another about the central longitudinal axis 30 as explained further below. Tip 16 comprises four tip protrusions 52 at 90° spaced radial locations about the axis 30 and four tip slots 53 alternatingly arranged with the tip protrusions.

The cutting window 42 depicted by way of example for distal tip 16 is non-parallel or angled relative to the central longitudinal axis 30, and the cutting window 42 extends from distal to proximal at an outward angle in a direction away from the axis 30. Accordingly, the external configuration of distal tip 16 in side view or longitudinal profile tapers in the distal direction from a proximal end of the cutting window 42 to a distal or forward end 56 of distal tip 16. The distal tip 16 comprises a cutting edge 54 along the peripheral edge of the cutting window 42 formed by way of example as a plurality of cutting teeth along the peripheral edge of the cutting window. However, the cutting window 42 can be provided without a cutting edge. The cutting teeth for cutting edge 54 are arranged on opposite sides of the axis 30 and extend from distal to proximal in side view or longitudinal profile so as to be non-parallel or angled to the axis 30 in accordance with the angle of the cutting window 42 as best shown in FIG. 3. The cutting window 42 is located distally of the forward edges of the tip protrusions 52, and the distal tip 16 terminates distally at the distal or forward end 56. The distal tip 16 and the body 18 are preferably made of a medically acceptable or biocompatible material such as stainless steel. The distal tip 16 is depicted as being integrally, unitarily or monolithically formed as a single piece or part such that the distal tip 16 is of one-piece construction. However, the distal tip 16 may be of multi-part construction for greater ease of manufacture and/or reduced cost as represented by the two-part distal tip shown in FIGS. 16 and 17.

The distal tip 16 is assembled to the elongate body 18 by being inserted, distal end 56 first, in the open proximal end of the body and pushed longitudinally distally or forwardly therein to extend distally from the open forward end of the body. With the body protrusions 36 longitudinally aligned with the tip slots 53 and the body slots 37 longitudinally aligned with the tip protrusions 52, the distal tip 16 can be maximally extended from the forward end of elongate body 18 in a longitudinally extended position for the outer member 12. The distance that the distal tip 16 extends from the forward end of the body 18 in the longitudinally extended position is limited or controlled due to engagement or abutment of the inwardly angled inner surfaces of the body protrusions 36 with the forward shoulder 46. In the longitudinally extended position, the body protrusions and slots 36 and 37 will be cooperatively interengaged with the tip slots and protrusions 53 and 52, respectively, with there being a tip protrusion 52 between each radially adjacent pair of body protrusions 36 to prevent relative rotation between the tip 16 and body 18 about the axis 30. Accordingly, the cutting window 42 will be locked in an initial one of the plurality of radial, angular or directional positions therefor about axis 30 and relative to bend 24 and will face in a predetermined direction relative to axis 30 and bend 24 corresponding to this radial, angular or directional position. The distal tip 16 will also be locked in one of a plurality of predetermined rotational positions for the distal tip about its axis 30 corresponding to the directional positions for cutting window 42, respectively.

The outer member 12 has a longitudinally retracted position in which the tip protrusions and slots 52 and 53 are disposed proximally of and thereby disengaged from the body slots and protrusions 37 and 36, respectively. The longitudinally retracted position is obtained via relative longitudinal movement between the distal tip 16 and body 18 whereby the tip is retracted relative to or within the body from the longitudinally extended position. Accordingly, the rearward end 40 of tip 16 is disposed closer to the forward end of body 18 in the longitudinally extended position than in the longitudinally retracted position. In the longitudinally retracted position, the tip 16 and body 18 are rotatable relative to each other about the axis 30, allowing the distal tip 16 to be rotationally indexed about its axis 30 to another predetermined rotational position in which the body protrusions and slots 36 and 37 are longitudinally aligned with the tip slots and protrusions 53 and 52, respectively. The another rotational position corresponds to another directional position for the cutting window 42 in which the cutting window faces in another predetermined direction relative to axis 30 and bend 24. In order to lock the distal tip 16 in the another rotational position, the outer member 12 is moved from the longitudinally retracted position to the longitudinally extended position to engage the body protrusions and slots 36 and 37 with the tip slots and protrusions 53 and 54, respectively, thereby preventing relative rotation between the distal tip 16 and elongate body 18 about axis 30.

The distal tip 16 is rotatable 360° about its axis 30 and is designed for four rotationally indexed positions corresponding to the 90° spaced radial locations for the body protrusions 36 and tip slots 53. However, the distal tip could be designed for any plurality of rotationally indexed positions about axis 30. The predetermined directional positions for cutting window 42 associated with the four rotational positions of tip 16 correspond to the cutting window facing upwardly, laterally, downwardly and medially, respectively, to axis 30 and the center of curvature R for bend 24, but could correspond to the cutting window facing in various other directions.

Inner member 14, which may be considered an inner blade member, is shown as being tubular but may be tubular or non-tubular. Inner member 14 has a proximal length region 58 extending distally from an inner member hub 60, a distal cutting tip 62 formed as or provided with a cutting edge 64 and a flexible or bendable region 66 between proximal length region 58 and cutting tip 62. The cutting tip 62 is adapted to cut anatomical tissue, and the cutting tip depicted by way of example for inner member 14 includes a cutting opening 68 communicating with a lumen 70 through the inner member and the cutting edge 64 extending along a peripheral edge of opening 68. The cutting edge 64 may be designed in various ways, for example as a plurality of cutting teeth along opposite sides of the peripheral edge of the cutting opening 68 as shown for inner member 14, and could also be designed as a burr. The cutting edge 64 and cutting opening 68 are non-parallel or angled to the central longitudinal axis of the inner member 14 as described for the cutting window 42.

Figure 9:
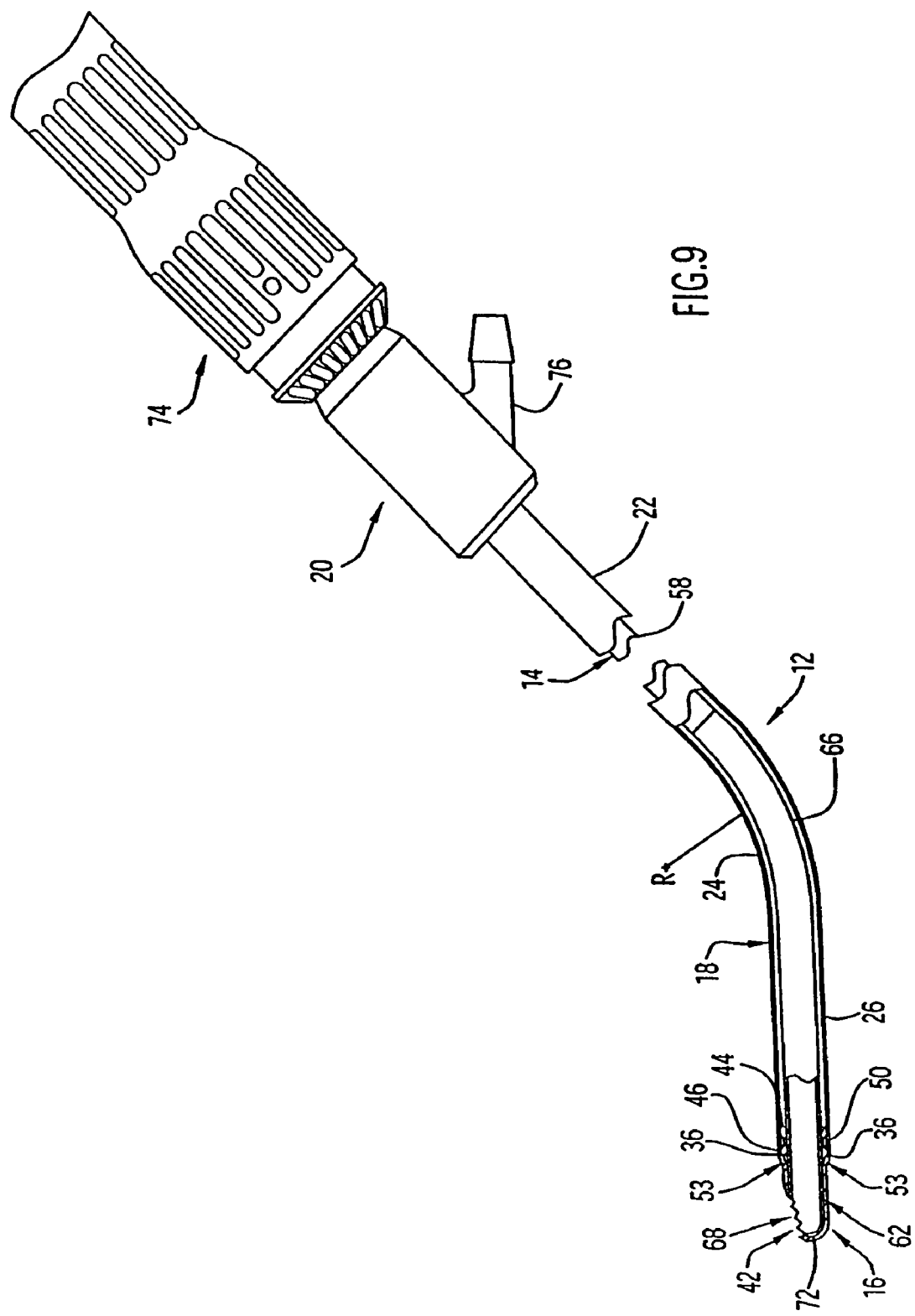
FIG. 9 is a broken longitudinal sectional view of the instrument depicting the outer member locked in a longitudinally extended position preventing relative rotation between the distal tip and the elongate body about a central longitudinal axis of the distal tip.

When the inner member 14 is disposed within the outer member 12 a maximum or full insertion distance as shown in FIGS. 1 and 9, the inner member extends through the outer member hub 20 with the inner member hub 60 disposed proximally of the outer member hub, the cutting edge 64 exposed by the cutting window 42 of distal tip 16, the distal outer surface of the cutting tip 62 in contact with the distal inner surface of distal tip 16 at a contact area 72, and the flexible region 66 disposed within or adjacent the bend 24 so that the inner member follows or conforms to the longitudinally or axially bent, curved or angled configuration of the outer member. Of course, the inner member 14 may include one or more flexible regions for being disposed in one or more bends of outer member 12. The length of the inner member 14 disposed in the lumen of outer member 12 to its full insertion distance places the outer member 12 in the longitudinally extended position due to the contact between the inner member and the outer member at contact area 72, and the inner member and outer member hubs 60 and 20 are connectible to a powered surgical handpiece 74 as depicted in FIGS. 1 and 9. Connection of the hubs 60, 20 to the handpiece 74 secures the inner member 14 to the outer member 12 with the inner member disposed the full insertion distance in the outer member and thereby locks the outer member in the longitudinally extended position with the distal tip 16 locked in a selected predetermined rotational position. In FIG. 9, the distal tip 16 is locked in a selected predetermined rotational position corresponding to a predetermined directional position for cutting window 42 in which the cutting window faces upwardly toward the center of curvature for the bend 24. The proximal length region 58 is rigid and transmits torque from the powered surgical handpiece 74 via the flexible region 66 to rotate the cutting tip 62 when the inner member 14 is rotated relative to and within the outer member 12 by the powered surgical handpiece. The flexible region 66 allows the inner member 14 to conform to the angled configuration of the outer member 12 as it is rotated relative to and within the outer member. The hubs 20 and 60 are adapted to be removably coupled with the powered surgical handpiece 74, and the powered surgical handpiece may be of the type disclosed in U.S. Pat. No. 5,916,231 to Bays, the entire disclosure of which is incorporated herein by reference. The handpiece could include a spring bias for the inner member hub by which the inner member 14 is resiliently biased distally to its full insertion distance within the outer member 12.

The cutting tip 62 can have various configurations depending on the surgical procedure to be performed and the type of cutting action. The cutting tip 62 accesses anatomical tissue at an operative site via the cutting window 42 of distal tip 16 and is aligned with or disposed adjacent the window 42 as the inner member 14 is rotated within the outer member 12. The distal tip 16 of the outer member 12 can be provided with or without a cutting edge and is shown as having cutting edge 54 cooperable with the cutting edge 64 of inner member 14 to cut anatomical tissue as the inner member is rotated within the outer member. The cutting edge 54 may be designed in various ways, for example as a sharp peripheral edge of window 42 or as a plurality of cutting teeth along the peripheral edge of window 42 as shown for outer member 12. The cutting edge 64 moves past the cutting edge 54 as the inner member is rotated within the outer member to cut anatomical tissue. When the cutting edge 64 coincides with the cutting window 42 as shown in FIG. 9, the angles of the cutting edge 64 and cutting window 42 coincide, such that the external longitudinal configuration or profile of the instrument corresponds essentially to the external longitudinal configuration or profile of the distal tip 16. Anatomical debris may be aspirated from the operative site through the lumen 70 of inner member 14, the opening 68 of the inner member forming a suction inlet through which debris is aspirated. Where the powered surgical handpiece of the aforementioned Bays patent is used, the debris is aspirated through the inner member and the handpiece. The flexible region 66 of the inner member 14 can be formed in various ways as represented by the RADenoid® blades of Medtronic Xomed Surgical Products and by U.S. Pat. No. 5,922,003 to Anctil et al, the entire disclosure of which is incorporated herein by reference. The inner member is preferably made of a medically acceptable or biocompatible material such as stainless steel.

Aspiration may be accomplished in the angled tissue cutting instrument through the inner member, through the outer member, such as between the outer member and the inner member, or in any other suitable manner. However, it should be appreciated that the angled tissue cutting instrument can be provided and/or used without aspiration. The angled tissue cutting instrument may be provided with or without an irrigation passage or channel for supplying irrigation or flushing fluid to the cutting site, and both aspiration and irrigation may be provided in the angled tissue cutting instrument. Irrigation may be provided along the instrument in various ways including internally through the inner member, internally through the outer member, such as between the outer member and the inner member, externally along the outer member, or in any other suitable manner. The angled tissue cutting instrument may include an external irrigation channel as disclosed in U.S. Pat. No. 5,782,795 to Bays and U.S. Pat. No. 6,312,438 B1 to Adams, the entire disclosures of which are incorporated herein by reference. The Adams patent is also representative of a burr tip which may be used as the cutting tip in the angled tissue cutting instrument and of an aspiration passage and aspiration port which may be incorporated in the inner member. The outer member hub 20 is illustrated with an optional nipple 76 providing an irrigation port in communication with the inlet port 32 of outer member 12 by which irrigation fluid may be supplied to the outer member lumen 38 for flow between the inner and outer members and discharge at the operative site via the cutting window 42. Leakage of irrigation fluid between the tip 16 and body 18 is prevented by seal 50.

Figure 10:
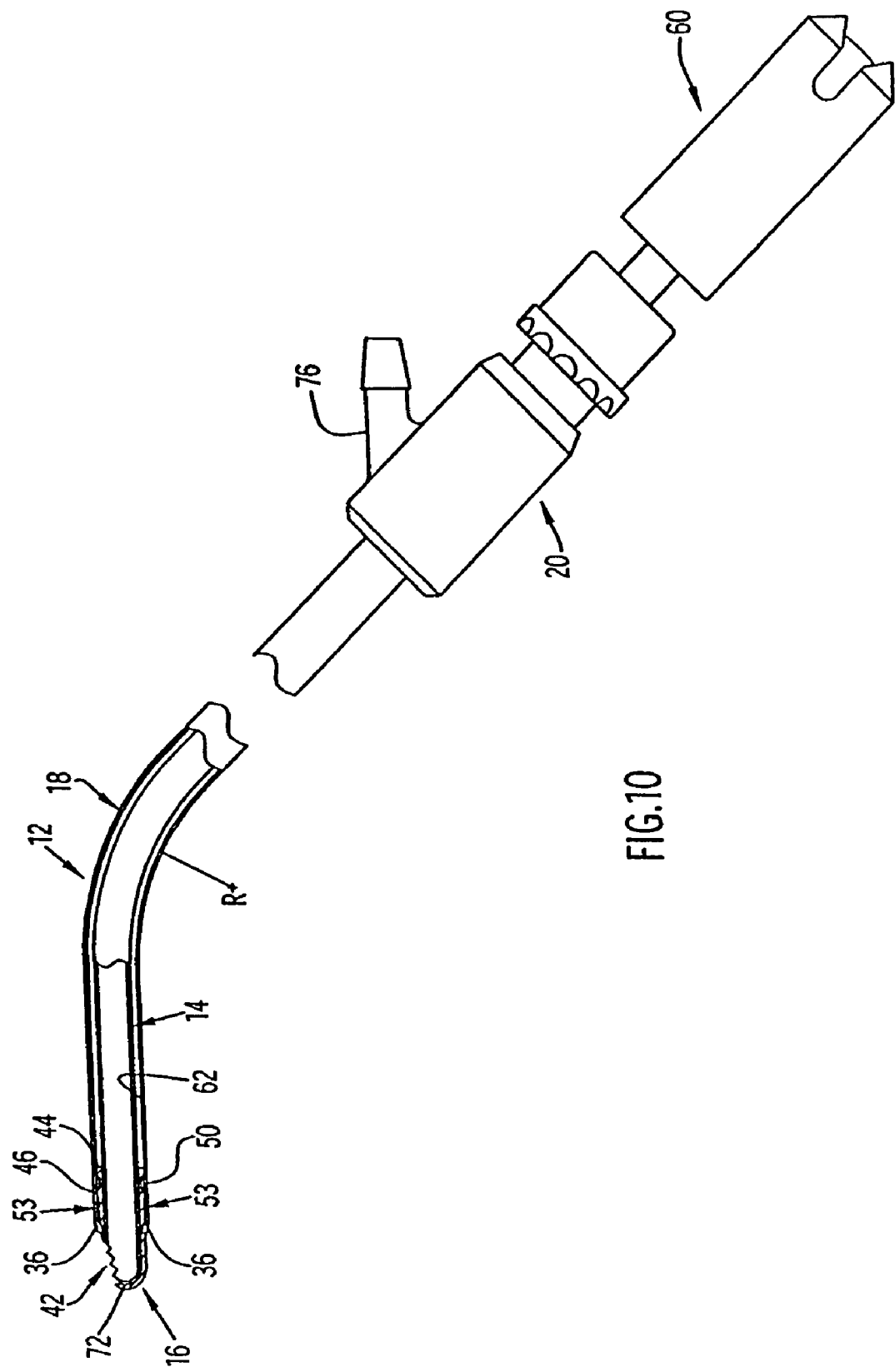
FIG. 10 is a broken longitudinal sectional view of the instrument depicting the outer member in a longitudinally retracted position permitting relative rotation between the distal tip and the elongate body about the central longitudinal axis to rotationally index the distal tip.

FIGS. 1, 2 and 9 illustrate the distal tip 16 in a first or initial predetermined rotational position and the cutting window 42 in a first or initial predetermined directional position in which the cutting window faces upwardly, i.e., toward the center of curvature R for the bend 24, which extends in a particular direction relative to or from the handpiece 74. To rotationally index the distal tip 16 and thereby vary the directional position of the cutting window 42 relative to the bend 24, the inner member 14 is withdrawn or moved proximally relative to the elongate body 18 of outer member 12 from its full insertion distance an amount sufficient to permit movement of the outer member from the longitudinally extended position to the longitudinally retracted position as shown in FIG. 10. Typically, the outer member 12 will be placed in the longitudinally retracted position by depressing the tip 16 longitudinally proximally relative to and toward the body 18 with a manually applied proximal axial force, such as that applied by a finger, or a mechanically applied force, such as that as applied by the indexing tool described below, while the body 18 is grasped. Withdrawing the inner member 14 proximally within the outer member 12 without removing the inner member entirely from the outer member allows the inner member to serve as a stop or abutment limiting the distance that the tip 16 may be retracted in the body 18 in the longitudinally retracted position so that a sufficient portion of the tip continues to extend from the forward end of the body to enable the tip to be manually or mechanically grasped. As shown in FIG. 10, the distal tip 16 contacts the cutting tip 62 at contact area 72 in the longitudinally retracted position so that the distal tip 16 is prevented from being retracted too far proximally within the body 18 and is prevented from being retracted entirely within the body. Depending on how the hubs 20 and 60 are mounted to the handpiece, it may be necessary to detach the hubs from the handpiece in order to withdraw the inner member 14 proximally relative to the elongate body 18. Withdrawal of the inner member 14 proximally relative to the elongate body 18 may be performed prior to moving the outer member 12 from its longitudinally extended position to its longitudinally retracted position or simultaneously with moving the outer member from its longitudinally extended position to its longitudinally retracted position. For example, the inner member 14 may be moved proximally relative to and within the elongate body 18 from its full insertion distance as a result of moving the distal tip 16 proximally relative to the elongate body 18 to obtain the longitudinally retracted position for the outer member 12. Where the handpiece spring biases the inner member 14 distally within the outer member 12, the inner member may be moved proximally from its full insertion distance while the inner and outer members remain attached to the handpiece and, therefore, the outer member may be moved from the longitudinally extended position to the longitudinally retracted position while the inner and outer members are attached to the handpiece.

When the outer member 12 is in the longitudinally retracted position, the body and tip protrusions 36, 52 are disengaged from the tip and body slots 53, 37, respectively, allowing rotational indexing of the distal tip 16 from the initial rotational position to a subsequent or another rotational position. In accordance with one manner of rotational indexing, the distal tip 16 is rotationally indexed by grasping the distal tip manually with the fingers or mechanically with a tool while the elongate body 18 is rotated relative to the tip about the axis 30, the inner member 14 conforming to the outer member 12 as the body 18 is rotated as shown in FIG. 10. Use of a tool to grasp the distal tip 16 is preferred in order to avoid hand contact with the sharp cutting edge or edges on or exposed from the distal tip and to avoid tearing of a surgical glove worn on the hand when contacting the distal tip. In another manner of rotational indexing described below, the distal tip 16 is rotated relative to the elongate body 18 while the elongate body is grasped.

FIG. 10 shows the distal tip 16 indexed to a subsequent rotational position 180° from the initial rotational position and in which the cutting window 42 is in a subsequent or another directional position 180° from the initial directional position with the window 42 facing in a direction away from the center of curvature R for the bend 24. Once the distal tip 16 has been rotationally indexed to the selected rotational position, the outer member 12 is moved from the longitudinally retracted position back to the longitudinally extended position as illustrated in FIG. 11 and as permitted due to longitudinal alignment of the protrusions 36, 52 with the slots 53, 37, respectively. Movement of the outer member 12 to the longitudinally extended position may be accomplished by advancing the inner member 14 distally within the outer member 12 to the full insertion distance whereby the tip 16 is maximally extended from the body 18 causing the body protrusions and slots 36 and 37 to cooperatively interengage with the tip slots and protrusions 53 and 52, respectively, to lock the distal tip in the subsequent rotational position. As the outer member 12 is moved from the longitudinally retracted position to the longitudinally extended position, there may be some relative rotation between the distal tip 16 and elongate body 18 as the tip and body engagement structure self-align to correct for misalignments when the distal tip is not indexed exactly to an established rotational position. Accordingly, rotational indexing of the distal tip 16 to a selected rotational position does not require that the distal tip 16 be rotated exactly to an established rotational position. Where the outer and inner members 12 and 14 have been detached from the handpiece, the outer and inner member hubs 20 and 60 are reattached to the handpiece 74 once the inner member 14 is advanced in the outer member 12 to the full insertion distance, thereby locking the outer member in the longitudinally extended position so that the distal tip 16 is locked in the subsequent rotational position as shown in FIG. 11. Where the outer and inner members 12 and 14 have not been detached from the handpiece, the spring bias provided by the handpiece on the inner member can be used to effect advancement of the inner member to its full insertion distance automatically when the proximal force on the distal tip 16 is removed. FIG. 11 shows the bend 24 again extending in the particular direction shown in FIG. 9 but with the cutting window 42 now facing downwardly, i.e., away from the center of curvature R for bend 24. Accordingly, the direction of the bend 24 in relation to the handpiece 74 may remain the same regardless of the rotational position selected for tip 16, and the orientation of the handpiece may remain the same for optimal grasping and manipulation by the surgeon.

Figure 14:
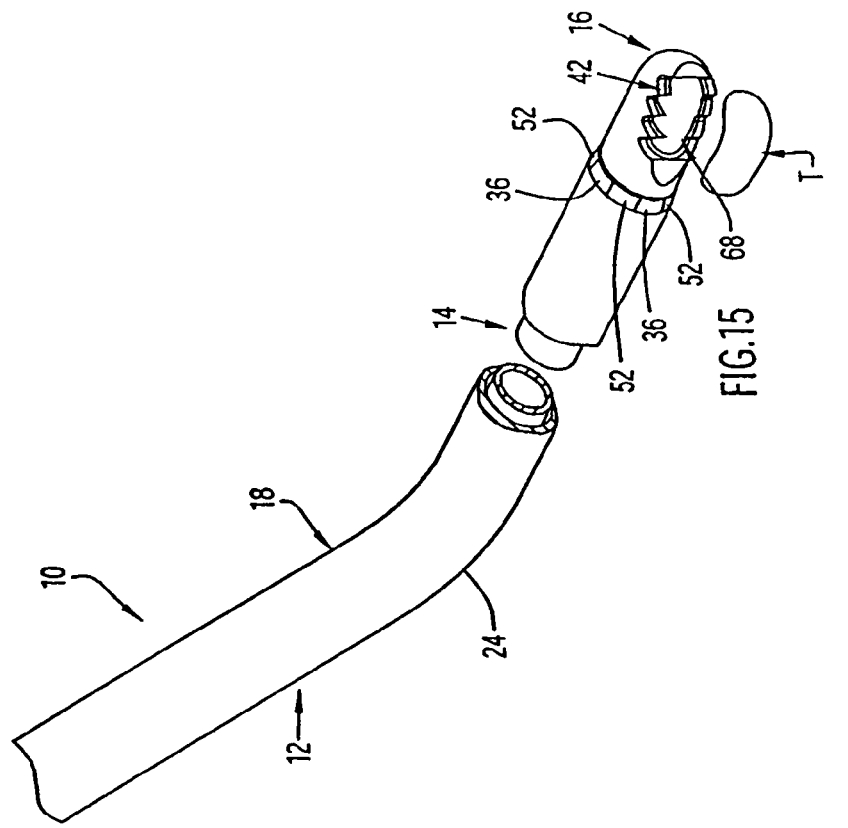
FIG. 14 is a broken perspective view showing the distal tip locked in a third rotational position about the central longitudinal axis.
Figure 15:
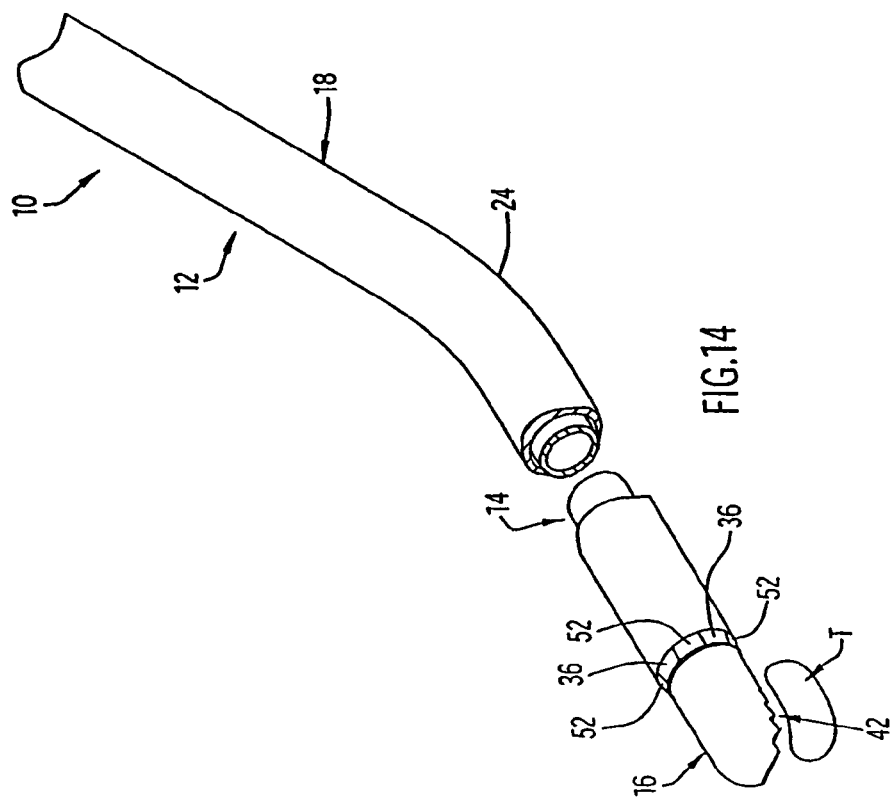
FIG. 15 is a broken perspective view depicting the distal tip locked in a fourth rotational position about the central longitudinal axis.

FIG. 12 illustrates the instrument 10 with the bend 24 extending in a particular direction to access an internal operative site and the distal tip 16 in a first rotational position with the cutting window 42 facing in the direction of the center of curvature for the bend in a first directional position for the cutting window. In this position, the cutting window 42 is optimally oriented to cut anatomical tissue T located superiorly or upwardly to the distal tip 16 while the bend 24 extends in the particular direction. FIG. 13 depicts the bend 24 extending in the particular direction with the tip 16 rotationally indexed to a second rotational position 90° clockwise from the first rotational position. The cutting window 42 is in a second directional position 90° clockwise from the first directional position and is optimally situated to cut anatomical tissue T located laterally/medially to the distal tip 16. FIG. 14 depicts the bend 24 extending in the particular direction but with the tip 16 rotationally indexed to a third rotational position 180° clockwise from the first rotational position and 90° clockwise from the second rotational position. The cutting window 42 is in a third directional position 180° clockwise from the first directional position and 90° clockwise from the second directional position and is optimally directed to cut anatomical tissue T located inferiorly or downwardly to the tip 16. The bend 24 is shown in FIG. 15 extending in the particular direction but with the tip 16 rotationally indexed to a fourth rotational position 270° clockwise from the first rotational position, 180° clockwise from the second rotational position, 90° clockwise from the third rotational position, and 90° counterclockwise from the first rotational position. The cutting window 42 is in a fourth directional position 270° clockwise from the first directional position, 180° clockwise from the second directional position, 90° clockwise from the third directional position, and 90° counterclockwise from the first directional position. In the fourth directional position, the cutting window 42 is optimally situated to cut anatomical tissue T medially/laterally to the tip 16. Although four rotational positions are shown for the distal tip 16 corresponding to four directional positions for cutting window 42 equally spaced 90° from one another about the central longitudinal axis 30, it should be appreciated that any suitable number of rotational and directional positions greater than one can be provided for the distal tip 16 and cutting window 42 at equally spaced or non-equally spaced radial, rotational or angular locations about the central longitudinal axis 30 of the distal tip 16. Depending on the manner in which the distal tip 16 is rotatably mounted to the forward end of body 18, the distal tip 16 and the body 18 may be rotated clockwise and/or counterclockwise to obtain the different rotational and directional positions.

In the illustrated embodiment, the distal tip 16 is locked in each rotational position with all of the protrusions 36, 52 engaged simultaneously in slots 53, 37, respectively. It should be appreciated, however, that the number of protrusions may be different than the number of slots so that not all of the slots and protrusions need to be interengaged when the distal tip 16 is locked in each rotational position. Although a plurality of protrusions is preferred, only one protrusion on the tip 16 or the body 18 may be necessary for engaging a selected one of a plurality of slots in the other of the tip 16 or the body 18, and any suitable number of slots may be provided for a single protrusion. Similarly, only one slot may be necessary on the tip 16 or the body 18 for engagement with a selected one of a plurality of protrusions on the other of the tip 16 or the body 18, and any suitable number of protrusions may be provided for a single slot. While the body protrusions 36 are located about the central longitudinal axis 30 at radial locations corresponding to the first, second, third and fourth rotational positions described for distal tip 16, the body slots 37 can alternatively be disposed at these locations. The protrusions and slots can be disposed at various locations, so long as each incremental rotational engagement of the distal tip 16 and the body 18 corresponds to a desired predetermined rotational, angular, radial or directional position for the cutting window 42. It should also be appreciated that any arrangement of the protrusions and slots can be reversed by substituting slots for the protrusions and substituting protrusions for the slots.

The angled tissue cutting instrument 10 can be used to access an internal operative site with the bend 24 extending in a particular direction and to cut anatomical tissue at the operative site located in different directions relative to the distal tip 16 and bend 24 depending on the rotational, radial, angular or directional position selected for the cutting window 42. Accordingly, the angled tissue cutting instrument 10 can be used for cutting in various directions relative to the bend without altering the bend or requiring that the orientation of the instrument be changed. With the angled tissue cutting instrument of the present invention, the rotational, radial, angular or directional position of the cutting window in the outer member about the central longitudinal axis of the distal tip can be selectively adjusted relative to the bend to position the window to face in various directions relative to the bend. The rotational positions for the distal tip can be equally spaced or non-equally spaced about the central longitudinal axis of the distal tip. The directional positions for the cutting window can be equally spaced or non-equally spaced about the central longitudinal axis of the distal tip. Cutting can be effected by the angled tissue cutting instrument via rotation, oscillation, or other movement of the inner member within the outer member.

Figure 16:
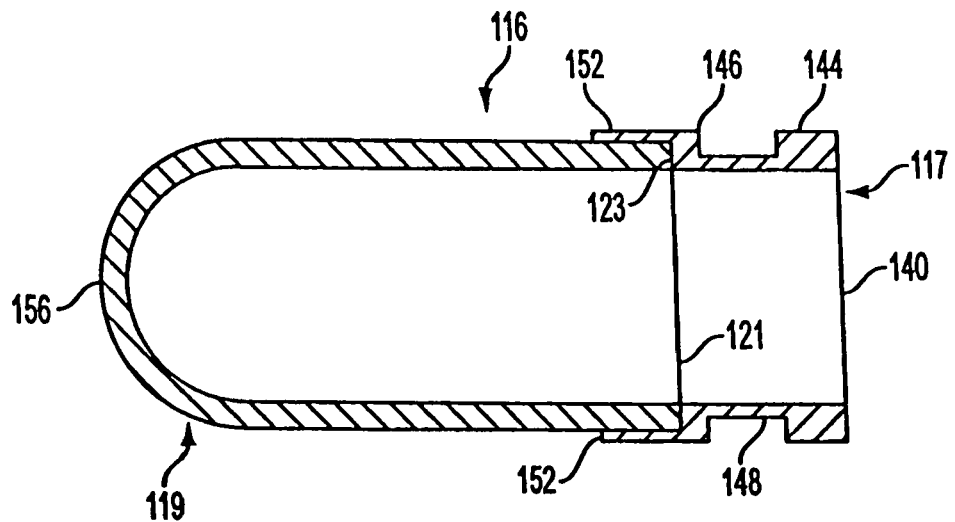
FIG. 16 is a top sectional view of an alternative distal tip of multi-part construction.
Figure 17:
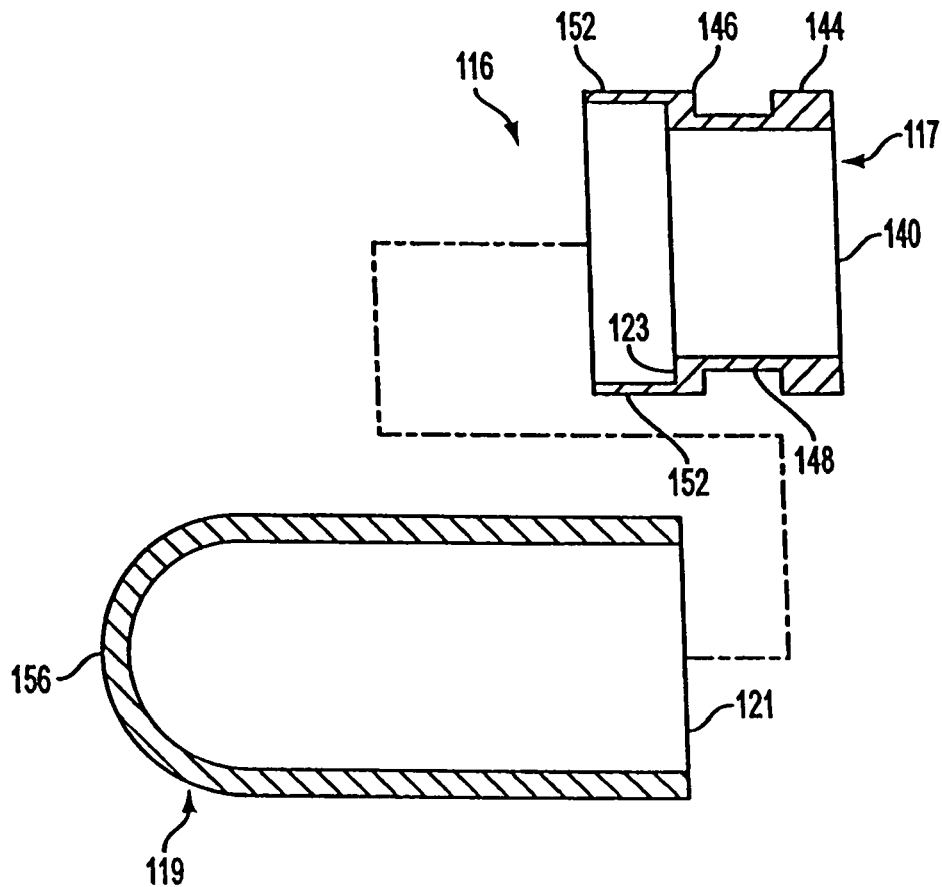
FIG. 17 is an exploded top sectional view of the alternative distal tip.

An alternative distal tip for use in the instrument 10 is illustrated at 116 in FIGS. 16 and 17. Distal tip 116 is similar to distal tip 16 but is of multi-part construction, the distal tip 116 being of two-part construction comprising a back part 117 and a front part 119. Back part 117, which is formed separately from the front part 119 as shown in FIG. 17, has a rearward annular shoulder 144 at rearward end 140 and forward annular shoulder 146 spaced longitudinally from rearward shoulder 144 by cylindrical segment 148. As described for tip 16, a seal may be disposed around cylindrical segment 148. The back part 117 includes a plurality of tip protrusions 152 extending longitudinally forwardly from the forward shoulder 146 and tip slots (not visible in FIGS. 16 and 17) between the tip protrusions 152. The tip protrusions 152 are spaced from one another at radial locations about the central longitudinal axis of the distal tip 116 and the distal length portion of the elongate body as described for the tip protrusions 52; however, the radial locations for tip protrusions 152 about the central longitudinal axis are different from the radial locations illustrated for tip protrusions 52. Four tip protrusions 152 may be provided in back part 117 at 90 degree spaced locations about the central longitudinal axis of the distal length portion of the body.

The front part 119 has the cutting window therein, which is not visible in the sectional views of FIGS. 16 and 17. The front part 119 has an open rearward end 121 received within an open forward end of the back part 117 with the rearward end 121 in abutment with an internal annular shoulder 123 of back part 117 as shown in FIG. 16. The back part 117 has a uniform inner diameter, and the front part 119 has a uniform inner diameter from internal shoulder 123 up to the curvature of forward end 156 that is the same or essentially the same as the inner diameter of the back part. The back part 117 can be fixedly secured in assembled relation with the front part 119 in any suitable manner. With the back part 117 and the front part 119 in assembled relation as shown by FIG. 16, the cutting window is disposed forwardly of the tip protrusions 152 and forwardly of the tip slots disposed between the tip protrusions 152. The tip protrusions 152 define raised keys along the outer surface of front part 119 distally or forwardly of the forward shoulder 146. As shown in FIG. 16, the tip protrusions 152 extend along the outer surface of front part 119 in contact therewith. As described for tip 16, the arcuate or circumferential width of the tip protrusions or keys 152 is selected to be received in the width of the body slots or keyways with a mating or complementary fit, and the arcuate or circumferential width of the tip slots or keyways is selected to receive the width of the body protrusions or keys with a mating or complementary fit to lock the distal tip 116 and the body against rotation relative to one another. The distal tip 116 may be preferred for ease of manufacturing and/or reduced cost, and the distal tip can be formed of two or more separate parts assembled together.

Figure 21:
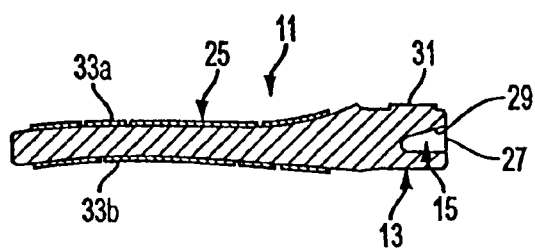
FIG. 21 is a side sectional view of the indexing tool.

An indexing tool 11 for use with the angled tissue cutting instrument 10 is illustrated in FIGS. 18-21. The indexing tool 11 is provided for moving the outer member 12 from the longitudinally extended position to the longitudinally retracted position and for rotationally indexing the retracted distal tip 16 relative to the elongate body 18 without the user's hand or fingers contacting the distal tip 16 and especially the cutting edge or edges on and/or exposed from the distal tip 16. The indexing tool 11 comprises a retention element 13 having a socket 15 for receiving a forward portion of distal tip 16 and a handle 25 extending from the retention element 13. The retention element 13 is cylindrical in external configuration from a first end of the retention element to a second end of the retention element connected to handle 25. However, the retention element 13 could have any suitable external configuration other than cylindrical. An entry opening 27 in the first end of the retention element 13 establishes communication with the socket 15 from externally of the indexing tool 11 for the insertion of distal tip 16 into the socket 15 through the entry opening 27. The entry opening 27 is coaxial with a central longitudinal axis of the retention element 13, and the socket 15 extends longitudinally in the retention element from the entry opening 27 to an internal end surface of the retention element. As best shown in FIG. 21, the socket 15 has a configuration to mate with the external longitudinal configuration or profile of the forward portion of distal tip 16 when the distal tip 16 is in a predetermined insertion orientation relative to the socket 15. In the case of distal tip 16, the longitudinal profile or configuration of the socket 15 tapers from the entry opening 27 toward the internal end surface of the retention member in accordance with the distal taper of the forward portion of distal tip 16. The retention element 13 thusly includes an angled internal surface 29 defining one side of socket 15 and extending longitudinally from entry opening 27 at an angle corresponding to the angle of cutting window 42. The angled internal surface 29 is disposed radial to the central longitudinal axis of the retention element 13, and the indexing tool 11 includes indicia 31 on an external surface of the retention element at the same radial location to the central longitudinal axis of the retention element as the angled internal surface 29. Accordingly, the indicia 31 is radially aligned with the angled internal surface 29.

The socket 15 removably receives the forward portion of distal tip 16 with a mating or complementary fit when the distal tip is inserted in the socket through entry opening 27 with the distal tip in the predetermined insertion orientation relative to the socket. When the distal tip 16 is not in the predetermined insertion orientation relative to the socket 15, the distal tip cannot properly be inserted into the socket with a mating fit. The distal tip 16 is inserted through entry opening 27 and placed deeper in the socket 15 with its central longitudinal axis 30 coaxially aligned with the central longitudinal axis of the retention element 13. The predetermined insertion orientation for the distal tip 16 in socket 15 corresponds to an orientation for the distal tip relative to the socket in which the cutting window 42 is aligned with the indicia 31 and is thusly at the same radial location to the aligned central longitudinal axes as the angled internal surface 29. Accordingly, regardless of the directional orientation of the cutting window 42 relative to the bend 24, the distal tip 16 can properly be inserted in the socket 15 with a mating fit only when the cutting window is in a particular predetermined orientation relative to the socket. The angled internal surface 29 assists in guiding the distal tip 16 into the socket 15 as the cutting window 42 is moved along the angled internal surface.

The indicia 31 is depicted as an arrow pointing toward the entry opening 27 and extending longitudinally along the retention element 13 parallel to the central longitudinal axis of the retention element. However, the indicia 31 could comprise any suitable symbolic and/or verbal identifiers. The indicia 31 points to the location of the entry opening 27 to facilitate insertion of the distal tip 16 in socket 15, identifies the radial location for the cutting window 42 to obtain the predetermined orientation needed for proper insertion of the distal tip in the socket, and depicts the longitudinal direction of movement for placement of the retention element over the distal tip 16 to position the distal tip in the socket. The indicia 31 is thusly multi-functional. The indicia 31 may be raised or elevated from the surrounding external surface of the retention element 13 to serve as both a visual and tactile indicator.

Figure 18:
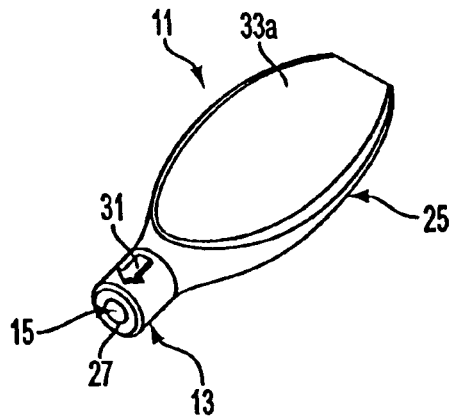
FIG. 18 is a perspective view of an indexing tool for the angled tissue cutting instrument.
Figure 19:
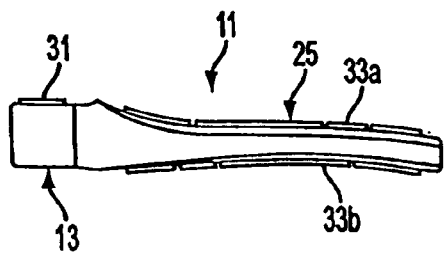
FIG. 19 is a side view of the indexing tool.
Figure 20:
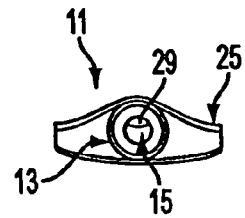
FIG. 20 is an end view of the indexing tool.

The handle 25 may have any suitable configuration to facilitate grasping by the hand of a user. The external surfaces of the handle may have raised lands configured as product labels and/or to facilitate grasping. The handle 25 has opposed grasping surfaces 33a and 33b presenting an ovoid peripheral configuration with a truncated end opposite the retention element 13 as shown in FIG. 18. The grasping surfaces 33a, 33b may have a gently curving convex curvature as illustrated in FIGS. 19 and 21 to facilitate grasping between the thumb and forefinger with the indicia 31 facing upwardly. The indexing tool 11 can be formed integrally, unitarily or monolithically as a single component and may be a machined or molded component. The indexing tool 11 may be made of medically acceptable plastic or any other suitable material and may be disposable for single patient use. The indexing tool 11 may be made available with sockets of various different sizes and/or various different configurations for various angled tissue cutting instruments of different distal tip sizes and/or configurations. It should be appreciated that the indexing tool 11 can be provided with a socket that is designed to accept different sizes and/or different configurations of distal tips.

Figure 22:
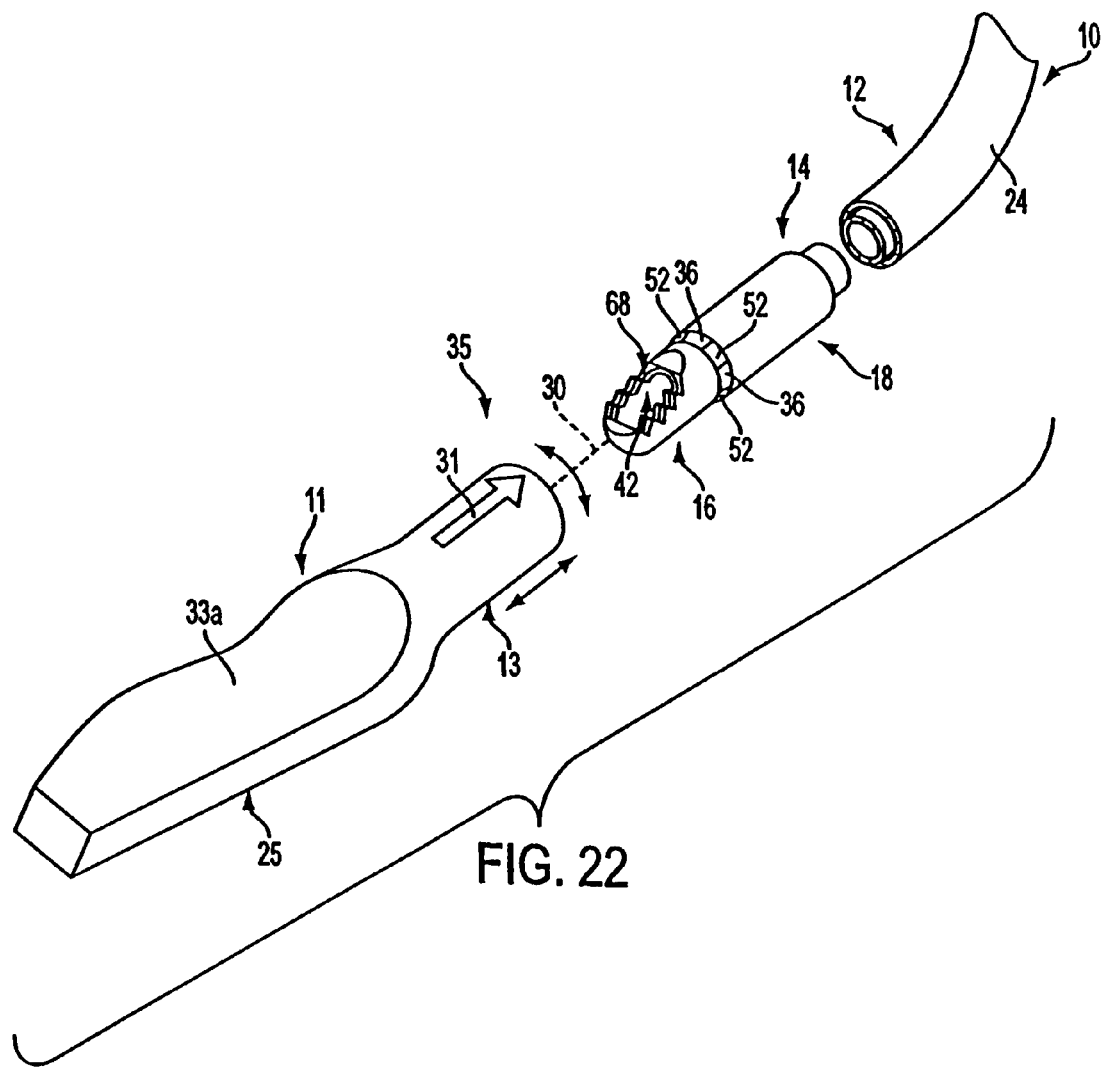
FIG. 22 is a broken perspective view illustrating an angled tissue cutting instrument kit comprising the indexing tool and the angled tissue cutting instrument and depicting use of the indexing tool to rotationally index the distal tip of the outer member of the angled tissue cutting instrument.

FIG. 22 depicts an angled tissue cutting instrument kit 35 comprising angled tissue cutting instrument 10 and indexing tool 11. The angled tissue cutting instrument 10 and indexing tool 11 may be supplied together in a package as kit 35 in a sterile condition ready for use in a surgical procedure. The indexing tool 11 may be used to move the outer member 12 from the longitudinally extended position to the longitudinally retracted position and to rotationally index the distal tip 16 of the outer member 12 when the outer member is in the longitudinally retracted position. To move the outer member 12 from the longitudinally extended position to the longitudinally retracted position mechanically using indexing tool 11, the elongate body 18 of outer member 12 is typically grasped in one hand and the handle 25 of indexing tool 11 is typically grasped in the opposite hand. The indexing tool 11 and/or the elongate body 18 is/are manipulated to place the distal tip 16, forward end 56 first, through the entry opening 27 and into the socket 15 with the distal tip in the predetermined insertion orientation relative to the socket. The distal tip 16 is placed in the socket 15 with its central longitudinal axis 30 coaxial with the central longitudinal axis of the retention element 13, with the distal tip being coaxially aligned with the retention element due to the entry opening 27 and internal surface 29 centering the distal tip 16 in the socket 15. The distal tip 16 is inserted in the socket 15 with the cutting window 42 aligned with the indicia 31 so as to be disposed at the same radial location to the aligned central longitudinal axes as the angled internal surface 29. The distal tip 16 is placed deeper into the socket 15 by moving the indexing tool 11 longitudinally toward the outer member 12 and/or by moving the outer member longitudinally along the central longitudinal axis 30 toward the indexing tool 11. The angled internal surface 29 of the socket 15 guides the distal tip 16 as it is placed in the socket and insures proper positioning of the distal tip in the socket. Placing the distal tip 16 deeper into the socket 15 causes the distal tip to engage the socket with a mating fit by which the retention element 13 may exert a proximal axial force against the distal tip 16 along the central longitudinal axis 30. Establishment of the mating fit is facilitated by alignment of the cutting edge and cutting opening 68 with the cutting window 42. The proximal force applied to the distal tip 16 by the indexing tool 11 along the central longitudinal axis 30 causes retraction of the distal tip 16 relative to the elongate body 18 to move the outer member 12 from the longitudinally extended position to the longitudinally retracted position, thereby disengaging the tip engagement structure from the body engagement structure to allow rotational indexing of the distal tip 16. Retraction of the distal tip 16 relative to the elongate body 18 may be preceded by the inner member 14 being moved proximally relative to the elongate body 18 from its full insertion distance, or the inner member 14 may be moved proximally from its full insertion distance by the distal tip 16 being retracted relative to the elongate body 18 as discussed above for manual or hand operation.

In order to rotationally index the distal tip 16 mechanically using the indexing tool 11 when the outer member 12 is in the longitudinally retracted position, the handle 25 is rotated to correspondingly rotate the retention element 13 about its central longitudinal axis which is coaxially aligned with the central longitudinal axis 30 of the distal tip 16 received in the socket 15. The retention element 13 applies rotational force to the distal tip 16 due to the mating fit of the distal tip in the socket 15, and the distal tip is thereby rotated about its central longitudinal axis 30 correspondingly with the retention element. As shown by an arrow in FIG. 22, the indexing tool 11 may be rotated clockwise or counterclockwise to rotationally index the distal tip 16 clockwise or counterclockwise to a desired rotational position corresponding to a desired directional position for the cutting window 42. Since the indicia 31 is located at the same radial position as the cutting window 42, the indicia serves as a marker indicating the radial position of the cutting window about the central longitudinal axis 30 as the distal tip 16 is rotationally indexed. Once the cutting window 42 has been rotated to the selected directional position, the outer member 12 is moved from the longitudinally retracted position back to the longitudinally extended position to lock the cutting window in the selected directional position and the indexing tool 11 is removed from the distal tip 16. The outer member 12 is moved from the longitudinally retracted position to the longitudinally extended position by advancing the inner member 14 distally within the outer member 12 to the full insertion distance. As discussed above, the inner member 14 may be advanced distally within the outer member 12 to the full insertion distance by manually inserting and advancing the inner member within the outer member or by mechanical spring pressure provided on the inner member by the handpiece. The indexing tool 11 can be removed from the distal tip 16 prior to or subsequent to moving the outer member 12 from the longitudinally retracted position to the longitudinally extended position. Use of the indexing tool 11 avoids contact of the user's hand or fingers with the distal tip 16 thereby avoiding the risk of tearing a surgical glove worn on the user's hand during a surgical procedure in which indexing of the distal tip is performed.

Inasmuch as the present invention is subject to various modifications, additions or changes in detail, the preferred embodiments described herein should be considered illustrative only and should not be taken in a limiting sense since various modifications can be made thereto without departing from the scope of the invention as defined by the appended claims.

What is claimed is:

1. An angled tissue cutting instrument comprising
an elongate outer member comprising an elongate body having a bend and a forward end and a distal tip rotatably mounted to said forward end, said distal tip including a central longitudinal axis and a cutting window having a directional position radial to said central longitudinal axis, said distal tip and said body being selectively rotatable relative to one another about said central longitudinal axis to move said cutting window to a different directional position radial to said central longitudinal axis; and
an elongate inner member movably disposed within said outer member and including a flexible region adjacent said bend and a cutting edge exposed from said cutting window for cutting anatomical tissue when said inner member is moved relative to and within said outer member.

2. The angled tissue cutting instrument recited in claim 1 wherein said inner member is rotatably disposed within said outer member.

3. The angled tissue cutting instrument recited in claim 1 wherein said inner member is removably disposed within said outer member.

4. The angled tissue cutting instrument recited in claim 1 wherein said cutting window is movable to a plurality of directional positions located at 90° spaced locations about said central longitudinal axis.

5. The angled tissue cutting instrument recited in claim 1 and further comprising means for releasably locking said cutting window in each of said directional positions.

6. The angled tissue cutting instrument recited in claim 5 wherein said distal tip includes tip engagement structure and said body includes body engagement structure selectively cooperatively interengageable with said tip engagement structure to lock said cutting window in each of said directional positions.

7. The angled tissue cutting instrument recited in claim 6 wherein said tip engagement structure includes at least one tip protrusion radial to said central longitudinal axis and said body engagement structure includes a plurality of body slots at radial locations about said central longitudinal axis, said at least one tip protrusion being selectively cooperatively interengageable with said body slots, respectively, to prevent relative rotation between said distal tip and said body about said central longitudinal axis when said cutting window is in each of said directional positions.

8. The angled tissue cutting instrument recited in claim 7 wherein said tip engagement structure includes a plurality of tip protrusions at radial locations about said central longitudinal axis and a plurality of tip slots each located between a pair of radially adjacent ones of said tip protrusions, and said body engagement structure further includes a plurality of body protrusions each located between a pair of radially adjacent ones of said body slots, said tip protrusions and said tip slots being selectively cooperatively interengageable with said body slots and said body protrusions, respectively, to prevent relative rotation between said distal tip and said body about said central longitudinal axis when said cutting window is in each of said directional positions.

9. The angled tissue cutting instrument recited in claim 6 wherein said tip engagement structure includes at least one tip slot radial to said central longitudinal axis and said body engagement structure includes a plurality of body protrusions at radial locations about said central longitudinal axis, said at least one tip slot being selectively cooperatively interengageable with said body protrusions, respectively, to prevent relative rotation between said distal tip and said body about said central longitudinal axis when said cutting window is in each of said directional positions.

10. The angled tissue cutting instrument recited in claim 1 wherein said bend comprises a rigid bend formed in said body.

11. The angled tissue cutting instrument recited in claim 6 wherein said distal tip comprises a back part and a front part assembled to said back part, said back part comprising said tip engagement structure and said front part comprising said cutting window.

12. The angled tissue cutting instrument recited in claim 6 wherein said distal tip is formed integrally unitarily as one piece.

13. An angled tissue cutting instrument comprising
an elongate outer member including an elongate body having a bend and a forward end and a distal tip mounted at said forward end, said distal tip including a central longitudinal axis and a cutting window facing in a direction transverse to said central longitudinal axis, said distal tip and said body being selectively rotatable relative to one another about said central longitudinal axis to rotationally index said distal tip to a plurality of rotational positions about said central longitudinal axis, said distal tip and said body being selectively movable longitudinally relative to one another between a longitudinally extended position for said outer member and a longitudinally retracted position for said outer member, said distal tip being releasably locked in a selected one of said rotational positions when said outer member is in said longitudinally extended position, and being unlocked from said selected rotational position when said outer member is in said longitudinally retracted position; and
an elongate inner member movably disposed within said outer member and including a flexible region adjacent said bend and a cutting edge exposed from said cutting window for cutting anatomical tissue when said inner member is moved relative to and within said outer member.

14. The angled tissue cutting instrument recited in claim 13 wherein said body includes a proximal length portion extending distally to said bend and a distal length portion extending from said bend to said forward end, said distal length portion being coaxial with said distal tip.

15. The angled tissue cutting instrument recited in claim 13 wherein said rotational positions are equally spaced about said central longitudinal axis.

16. The angled tissue cutting instrument recited in claim 15 wherein said cutting window has a plurality of directional positions about said central longitudinal axis corresponding to said rotational positions, respectively.

17. The angled tissue cutting instrument recited in claim 13 wherein said bend is rigid and said inner member is rotatably disposed within said outer member.

18. The angled tissue cutting instrument recited in claim 13 and further comprising tip engagement structure on said distal tip and body engagement structure on said body, said body engagement structure being cooperatively interengaged with said tip engagement structure when said outer member is in said longitudinally extended position to prevent relative rotation between said distal tip and said body about said central longitudinal axis and being disengaged from said tip engagement structure when said outer member is in said longitudinally retracted position to permit relative rotation between said distal tip and said body about said central longitudinal axis.

19. The angled tissue cutting instrument recited in claim 18 wherein said tip engagement structure and said body engagement structure are located at 90° spaced radial locations about said central longitudinal axis.

20. The angled tissue cutting instrument recited in claim 18 wherein said distal tip includes a rearward end slidably disposed in a forward end of said body.

21. The angled tissue cutting instrument recited in claim 20 wherein said distal tip is formed monolithically as a single part.

22. The angled tissue cutting instrument recited in claim 20 wherein said tip engagement structure is formed on a back part of said distal tip and said cutting window is formed in a front part of said distal tip, said front part having a rearward end fixedly secured in a forward end of said back part, said back part having a rearward end defining said rearward end of said distal tip.

23. An angled tissue cutting instrument comprising
an elongate outer member including an elongate body having a proximal end, a forward end and a bend between said proximal end and said forward end, and a distal tip mounted to said forward end, said distal tip having a central longitudinal axis and a cutting window facing transverse to said central longitudinal axis, said distal tip and said body being selectively rotatable relative to one another about said central longitudinal axis to locate said distal tip at a plurality of rotational positions about said central longitudinal axis;
an elongate inner member rotatably disposed within said outer member and having a maximum insertion distance within said outer member wherein a cutting edge of the inner member is exposed from said cutting window for cutting anatomical tissue when said inner member is rotated relative to and within said outer member, said inner member being movable proximally from said maximum insertion distance, said distal tip being locked in one of said rotational positions when said inner member is disposed said maximum insertion distance within said outer member and being unlocked from said one of said rotational positions when said inner member is moved proximally from said maximum insertion distance.

24. The angled tissue cutting instrument recited in claim 23 wherein said distal tip and said body are movable longitudinally relative to one another between a longitudinally extended position for said outer member and a longitudinally retracted position for said outer member, said distal tip and said body being prevented from rotating relative to one another about said central longitudinal axis in said longitudinally extended position and being permitted to rotate relative to one another about said central longitudinal axis in said longitudinally retracted position, said outer member being maintained in said longitudinally extended position in response to said inner member being disposed said maximum insertion distance within said outer member and being movable to said longitudinally retracted position in response to said inner member being moved proximally from said maximum insertion distance.

25. The angled tissue cutting instrument recited in claim 24 wherein said distal tip is maximally extended distally from said body in said longitudinally extended position and is retracted proximally relative to said body in said longitudinally retracted position.

26. The angled tissue cutting instrument recited in claim 24 wherein said distal tip includes tip engagement structure and said body includes body engagement structure engaged with said tip engagement structure to prevent relative rotation between said distal tip and said body about said central longitudinal axis in said longitudinally extended position and disengaged from said tip engagement structure to permit relative rotation between said distal tip and said body about said central longitudinal axis in said longitudinally retracted position.

27. The angled tissue cutting instrument recited in claim 23 wherein said distal tip includes tip engagement structure and said body includes body engagement structure engaged with said tip engagement structure when said inner member is disposed in said outer member said maximum insertion distance to prevent relative rotation between said distal tip and said body about said central longitudinal axis and disengaged from said tip engagement structure when said inner member is moved proximally from said maximum insertion distance to permit relative rotation between said distal tip and said body about said central longitudinal axis.

28. The angled tissue cutting instrument recited in claim 23 wherein said inner member includes a proximal end and further including a handpiece connectible to said proximal end of said outer member and said proximal end of said inner member to secure said inner member within said outer member said maximum insertion distance.

29. An indexing tool for an angled tissue cutting instrument having an inner member disposed in an outer member including an elongate body and a distal tip having a cutting window, comprising
    a retention element having a central longitudinal axis and a socket for removably receiving the distal tip of the outer member of the angled tissue cutting instrument, said socket having a configuration to mate with an external configuration of the distal tip when the distal tip is in an insertion orientation relative to said socket;
    external indicia alignable with the cutting window of the distal tip to obtain the insertion orientation for the distal tip relative to said socket; and
    a handle extending from said retention element, said handle being movable to move said retention element longitudinally along said central longitudinal axis to apply axial force to the distal tip received in said socket by which the distal tip is retracted proximally relative to the elongate body and to move said retention element rotationally about said central longitudinal axis to apply rotational force to the retracted distal tip received in said socket by which the distal tip is rotated relative to the elongate body.

30. The indexing tool recited in claim 29 wherein said indicia is located on said retention element radial to said central longitudinal axis.

31. The indexing tool recited in claim 30 wherein said indicia comprises an arrow extending parallel to said central longitudinal axis.

32. The indexing tool recited in claim 29 wherein said configuration of said socket mates with the external configuration of the distal tip with said central longitudinal axis of said retention element coaxially aligned with a central longitudinal axis of the distal tip.

33. The indexing tool recited in claim 31 wherein said arrow is raised from an external surface of said retention element.

34. An angled tissue cutting instrument kit comprising
    an angled tissue cutting instrument including an elongate outer member and an elongate inner member movably disposed in said outer member, said outer member comprising an elongate body having a bend and a forward end and a distal tip mounted on said forward end, said distal tip having a central longitudinal axis and a cutting window radial to said central longitudinal axis, said distal tip being movable longitudinally relative to said elongate body from a longitudinally extended position to a longitudinally retracted position in response to axial force on said distal tip, said distal tip being rotatable relative to said elongate body about said central longitudinal axis in said longitudinally retracted position to adjust the radial position of said cutting window about said central longitudinal axis in response to rotational force on said distal tip, said distal tip being prevented from rotating relative to said elongate body about said central longitudinal axis in said longitudinally extended position to lock said cutting window in a selected radial position about said central longitudinal axis; and
    an indexing tool comprising a retention element having a socket for removably receiving said distal tip and a handle extending from said retention element, said indexing tool being movable via said handle to apply said axial force and said rotational forces on said distal tip.

35. The angled tissue cutting instrument kit recited in claim 34 wherein said distal tip has an external configuration and said socket has a configuration to mate with said external configuration of said distal tip.

36. The angled tissue cutting instrument kit recited in claim 35 wherein said distal tip mates with said socket when said distal tip is in an insertion orientation relative to said socket and does not mate with said socket when said distal tip is not in said insertion orientation.

37. The angled tissue cutting instrument kit recited in claim 36 wherein said indexing tool further comprises external indicia and said insertion orientation corresponds to alignment of said cutting window with said indicia.

38. The angled tissue cutting instrument kit recited in claim 37 wherein said retention element has a central longitudinal axis, said distal tip mates with said socket with said longitudinal axis of said distal tip coaxial with said central longitudinal axis of said retention element, and said indicia is disposed on said retention element radial to said central longitudinal axis of said retention element.

39. The angled tissue cutting instrument kit recited in claim 38 wherein said retention element comprises an arrow parallel to said central longitudinal axis of said retention element.

40. The angled tissue cutting instrument kit recited in claim 34 wherein said retention element and said handle are formed monolithically as a single component.

41. The angled tissue cutting instrument kit recited in claim 34 wherein said cutting window is angled relative to said central longitudinal axis of said distal tip and said socket is partly defined by an angled internal surface of said retention element having an angle corresponding to the angle of said cutting window.

42. The angled tissue cutting instrument kit recited in claim 41 wherein said retention element includes a central longitudinal axis, said angled internal surface is radial to said central longitudinal axis of said retention element and said retention element further comprises external indicia radially aligned with said angled internal surface.

\* \* \* \* \*